United States Patent [19]
Kokusho et al.

[11] Patent Number: 5,190,868
[45] Date of Patent: Mar. 2, 1993

[54] CONTINUOUS PROCESS FOR THE INTERESTERIFICATION OF FATS OR OILS

[75] Inventors: Yoshitaka Kokusho, Kunitachi; Akio Oshima, Hino; Akira Tsunoda, Hino; Shinjiro Iwasaki, Hino, all of Japan

[73] Assignee: Meito Sangyo Co., Ltd., Nagoya, Japan

[21] Appl. No.: 644,425

[22] Filed: Jan. 22, 1991

Related U.S. Application Data

[63] Continuation of Ser. No. 238,072, Aug. 30, 1988, abandoned.

[30] Foreign Application Priority Data

Aug. 31, 1987 [JP] Japan ................. 62-215508
Jun. 30, 1988 [JP] Japan ................. 63-162930

[51] Int. Cl.$^5$ .......... C12P 7/64; C12P 7/62; C12N 11/14; C12N 9/20
[52] U.S. Cl. .................. 435/134; 435/134; 435/176; 435/177; 435/198
[58] Field of Search .............. 435/134, 135, 176, 177, 435/198

[56] References Cited

U.S. PATENT DOCUMENTS

| | | | |
|---|---|---|---|
| 4,275,081 | 6/1981 | Coleman et al. | 435/134 |
| 4,283,494 | 8/1981 | Kokusho et al. | 435/198 |
| 4,416,991 | 11/1983 | Matsuo et al. | 435/134 |

FOREIGN PATENT DOCUMENTS

183691 10/1984 Japan ................. 435/198

OTHER PUBLICATIONS

Kato et al, *J of Chromatography*, vol. 245, 1982, pp. 193–211.

*Primary Examiner*—David M. Naff
*Assistant Examiner*—Michael V. Meller
*Attorney, Agent, or Firm*—Armstrong, Westerman, Hattori, McLeland & Naughton

[57] ABSTRACT

Disclosed is a process for the interesterification of oil or fat by treating such oil or fat in presence of a fatty acid or fatty acid ester or different oil or fat wherein a reactor column that is packed with an alkaline high molecular weight lipase preparation containing 0 to 5% moisture is fed with a substrate solution composed of the above oil or fat and fatty acid or fatty acid ester or different oil or fat for a continuous reaction in such a manner that the substrate solution contains 100 to 1800 ppm moisture and 50 to 800 ppm moisture at the inlet and outlet, respectively, of the column.

13 Claims, 1 Drawing Sheet

CONTINUOUS PROCESS FOR THE INTERESTERIFICATION OF FATS OR OILS

This application is a continuation of application Ser. No. 238,072 filed Aug. 30, 1988, now abandoned.

BACKGROUND OF THE INVENTION

1. Field of the Invention

This invention relates to a process for the production of interesterified glyceride oil or fat of high added value at cheap cost by the continuous interesterification of glyceride oil or fat in presence of a fatty acid, fatty acid ester or different glyceride oil or fat.

More specifically, the invention relates to an efficient process of the interesterification of glyceride oil or fat wherein the reaction is continuously performed without need of any dehydration in a reactor column packed with an alkaline high molecular weight lipase preparation capable of continuously and strongly catalyzing the interesterification of glyceride oil or fat in presence of a fatty acid, fatty acid ester or different glyceride oil or fat in such a very low moisture content condition that no reaction of this sort has hitherto been considered possible.

2. Description of the Prior Art

The interesterification of glyceride oils and fats is an effective means to modify the chemical composition and physical properties of these oils and fats for upgrading.

Both chemical and enzymatic processes are known for the interesterification. The chemical process of interesterification is carried out at high temperatures in presence of an inorganic catalyst, such as sodium metal or sodium methylate, and applied to the production of margarine, shortening, and other processed oils and fats.

However, the chemical process of interesterification not only requires severer reaction conditions as compared to the enzymatic process but is nonspecific to the positions of the triglyceride molecule and therefore applicable only to randomization. Accordingly, interesterified oils and fats thereby produced are upgraded and add values only to a limited degree. By contrast, in the enzymatic process of interesterification, the reaction proceeds in mild conditions and use of a position specific lipase can limit interesterification to a selected glyceride position or positions, so more added values can be expected with interesterified oils and fats. Many studies have thus been made in this field.

Japanese Patent Opening 52-104506 (Unilever) and others proposed a number of batch processes, each making use of an acidic or neutral lipase of low molecular weight from *Rhizopus*, *Aspergillus* or *Mucor* source. However, many of these proposed batch processes use a method in which the lipase can be activated only when aqueous solution of this enzyme is concentratively carried as such by a porous carrier, for example, activated carbon or celite. For water that is practically involved in the reaction system of these proposed processes, beside the aqueous solvent from the specified substrate solution, water that leaks out of the enzyme support provides a practically abundant additional water supply to the reaction system. Further, the above additional water supply adds with a large quantity of support used at every reaction batch and it is such additional water supply that gives rise to the intended reaction. The process proposed by the present invention is essentially different from these disclosures in this point.

On the one hand, continuous processes of the enzymatic interesterification are disclosed in European Patent Publication 0140542, Japanese Patent Opening 61-202688 (Novo), European Patent Publication 0170431, and European Patent Publication 0069599 (Unilever). In the processes disclosed by these patents, an acidic or neutral lipase of low molecular weight from *Mucor*, *Aspergillus* or *Rhizopus* source is used. The above enzyme is used as an enzyme preparation supported in the form of aqueous enzyme solution by a support such as CELITE. Or alternatively, the enzyme is immobilized on an adsorbent resin or ion exchange resin by adsorption and the resultant immobilized enzyme preparation is adjusted to a specified moisture content. Different from the very low moisture content range of the substrate solution as specified by the present invention, the above processes are characterized by the continuous reaction that occurs in abundant presence of aqueous solvent. Of the above disclosures, only Japanese Patent Opening 61-202688 explicitly describes about the moisture content of the substrate though only giving data for the moisture content of the substrate at the outlet of the reactor column. Namely, this patent specifies 3600 to 5000 ppm and 2800 to 3100 ppm moisture for the substrate output from the reactor column at the initial stage of reaction and after 400 hr continued reaction, respectively. Thus, the present invention definitely differs from the above disclosure in the following point. Namely, while in a trace moisture range as specified by this invention the alkaline high molecular weight lipase catalyzes interesterification strongly in a continuous process of long period, the low molecular weight lipase as disclosed in the above disclosure can effect almost no interesterification in such a trace moisture range. On the other hand, in the moisture range specified for the continuous reaction in the above disclosure, though the low molecular weight lipase may effect interesterification fully, the moisture is too high to have the alkaline high molecular weight lipase efficiently and satisfactorily catalyze the continuous interesterification process.

OBJECTS AND SUMMARY OF THE INVENTION

The present authors already discovered an efficient process of interesterification of oil or fat in presence of a fatty acid, fatty acid ester, or different oil or fat wherein an alkaline high molecular weight lipase as produced by *Alcaligenes*, *Achromobacter*, or *Pseudomonas* bacteria is used to catalyze a reaction started in presence of a moisture-containing organic solvent with gradual dehydration effected after accumulation of diglycerides up to a given level (Japanese Patent Application 62-45302). The above process was described with reference to a batch process of interesterification but no continuous process of interesterification was indicated therewith.

Namely, to have the reaction proceed for the batch process of interesterification as disclosed by the above patent, it is necessary to gradually remove the initially added water from the reaction system from the middle to the end stage of the reaction. This requires, for example, bubbling the reaction system with dry nitrogen gas. For materialization of such operation at the industrial scale, however, there are many mechanical problems to be solved. Further, such dehydration adds an expensive cost. Among others, it should be unavoidable to use equipment of more complicated design and larger scale. It is thus expected that even if consideration is limited to the reactor tank, equipment about 100 times or larger in size would be necessary as compared to the continuous process. Thus, the above batch process is rather uneconomical and not always suitable to mass production. Another weak point of the batch process of interesterification is a slower reaction rate. The primary cause of such weak point is a comparatively high moisture content required in the batch process that needs dehydration. It is thus unavoidable to have a long reaction time for interesterification with the rate of mechanical dehydration determining the rate of interesterification. Further, to expedite the rate of reaction in the batch process, it is necessary not only to use a satisfactory quantity of the enzyme but bring the substrate in closer contact to the enzyme by agitation. With mechanical agitation method that is limited in efficiency, however, the rate of reaction cannot be increased sufficiently high. In addition, forces applied for agitation gradually break support of the immobilized enzyme, posing the problem of short life of the support itself.

Accordingly, the present authors studied ardently for development of a continuous process of interesterification suitable to the mass production of interesterified oils and fats. Surprisingly, it was found that the same alkaline high molecular weight lipases as used in the above batch process of interesterification are enzymes that are very suitable to apply to the continuous process of interesterification. Namely, a finding was made that if a substrate material is continuously passed together with a constant supply of trace water that is necessary for the reaction across a reactor packed with an alkaline high molecular weight lipase preparation, interesterification proceeds at a high rate for a prolonged duration of time without requiring any dehydration. Compared to the batch process of interesterification as mentioned above, the above continuous process of interesterification has many merits, for example, a much faster rate of reaction and need of just trace water for the reaction, with no need of both dehydration and agitation, operations that would break the carrier of immobilized enzyme.

Based on the above new finding, the authors used the aforementioned alkaline high molecular weight lipase that is characterized as interesterification enzyme by such superior properties as never seen before in the immobilized form to develop a very efficient continuous process of interesterification in presence of moisture of such a trace level that is even lower than the low moisture range proposed before. This led to the completion of the invention.

The invention provides a process for the interesterification of glyceride oil or fat by treating such oil or fat in presence of a fatty acid or fatty acid ester or different glyceride oil or fat wherein a reactor column that is packed with an alkaline high molecular weight lipase preparation containing 0 to 5% moisture is fed with a substrate solution composed of raw material oil or fat and fatty acid or fatty acid ester or different oil or fat for a continuous reaction in such a manner that the substrate solution contains 100 to 1800 ppm and 50 to 800 ppm moisture at the inlet and outlet, respectively, of the column. It is noted that though in the above description the high molecular weight lipase preparation can theoretically contain a moisture content as low as 0%, the lower limit to the moisture content is actually about 0.1% or more since such trace water is unavoidably contained by the enzyme preparation.

Preferably for the above alkaline high molecular weight lipase are enzymes from microbial sources characterized by the 1,3 positional specificity, molecular weight of 100,000 or over, and optimum pH of 8.0 or over. The alkaline high molecular weight lipase is used either in the unbound form or in the immobilized form bound to ion exchange resin, proteins, sugars, or mineral clay. A preferable example of the ion exchange resin is weak acidic methacrylate ion exchange resin. As a means to adjust the moisture content of alkaline high molecular weight lipase preparation between 0 and 5%, freeze drying is preferable. The interesterification normally proceeds at temperatures not higher than 80° C.

Isolation and refining of the reaction product is preferably performed as follows.

The interesterified oil or fat as produced by the continuous process of interesterification is removed and recovered from the reaction solution by a combination of methods, such as precipitation by cooling, distillation, neutralization, filtration across membrane, solvent fractionation, etc. As a general procedure, the reaction solution discharged from the reactor column is cooled as it is or after neutralization to precipitate components of higher melting points for simple fractionation. It is noted that solvent can be removed as necessary beforehand from the reaction solution, for example, by distillation or filtration across membrane to perform the above operations with the solvent-free oil or fat residue as it is or after redissolved in new solvent. Namely, the reaction solution containing interesterified oil or fat is cooled down to precipitate and remove components of high melting points therefrom. Or the solvent used for the reaction is removed from the reaction solution under reduced pressure or by filtration across membrane to recover solvent-free interesterified oil or fat, which can be redissolved in an organic solvent and cooled down for isolation of refined interesterified oil or fat. In case the reaction solution containing interesterified oil or fat contains fatty acid contaminants, an alkali agent is added to the solution to convert the fatty acids into soap for removal. Or the above solvent-free oil or fat fraction can be distilled to get fatty acid-free oil or fat. Further, the fatty acid-free oil or fat can be dissolved in an organic solvent and cooled down for precipitation and fractionation to get the refined product. The interesterified oil or fat fraction that either precipitates from or remains in the solution is distilled or subjected to solvent fractionation as necessary to remove contaminants to get target oil or fat in the refined form.

As compared to the batch process as disclosed in Japanese Patent Application 62-45302, the continuous process of the invention for production of interesterified oils and fats needs even less water for the reaction system requiring no additional control mechanism for dehydration to adjust the moisture content during the reaction. This means a simpler design of equipment. Besides, the above continuous process has such a merit that the reaction is faster and rather free from hydrolysis that produces side-products like diglycerides. Further, since the activity loss of an enzyme is generally proportional to the moisture content used, the process wherein the reaction proceeds in presence of just trace water from beginning to end can keep the enzyme stable for longer service.

TABLE 1-continued

| Lipase (source) | M.W. (×10³) | Opt. pH | References |
|---|---|---|---|
| Geotrichum candidum | 54.0 | 6.0 | |
| Rhizopus arrhizus | 43.0 | 7.0 | Jozo Kyokai-shi 73(8) 601 (1978) |
| Mucor javanicus | 27.5 | 7.0 | |
| Mucor miehei (NOVO sp 225) | 30–40* | 7.0 | NOVO Enzyme Information 1B-number 299a-GB-a (Sept., 1983) |
| Invention: | | | |
| Lipase PL-266 | 180–190 | 9.5–10.5 | JPP 58-36953 |
| Lipase PL-679 | 350–370 | 8.5–9.0 | JPP 60-15312 |
| Lipase AL | 350–400 | 10.0 | JPP 49-32080 |
| Lipase PS | 500 | 9.5 | Abstract of Papers for 1976 Conference of Japan Society of Agricultural Chemistry, p.334; (PH) Agric. Biol. Chem., 41, 1353 (1977) |

*The molecular weight of Mucor miehei lipase was determined by chromatography on Sephadex G-100 column 20 × 600 mm, 50 mM phosphate buffer (pH 7.5) and flow rate of 30 mL/hr.

The reason why the alkaline high molecular weight lipases as used in the invention exerts superior catalytic activities in the interesterification particularly in presence of just trace water as compared to the conventional lipases proposed could be that with these alkaline high molecular weight lipases the subunit structure and attached protein molecule not only protect the active site of lipase but abundantly carry intramolecularly bound moisture which might play some facilitating role in the development of enzymatic activity in the trace water reaction system.

The following experiment was made to give some idea of the differences of the high molecular weight lipase and low molecular weight one in the esterifying activity in a trace water reaction system.

Experiment 1 - Comparison of lipases in the esterifying activity in a trace water reaction system.

Lipase PL-679 (supplier: Meito Sangyo, specific activity: 87,000 U/g), Lipase PL-266 (Meito Sangyo Co., Ltd., 11,000 U/g), Lipase AL (Meito Sangyo Co., Ltd., 15,000 U/g), Lipase PS (Sappro Breweries Co., Ltd., 16,000 U/g), Talipase or Rhizopus delemar lipase (Tanabe Seiyaku Co., Ltd., 10,000 U/g), Lipase AP or Aspergillus niger lipase (Amano Seiyaku Co., Ltd., 37,000U/g), Lipase NOVO sp 225 or Mucor miehei lipase (NOVO, nominal 210,000 U/g ) were tested in this experiment. 100 mg samples of powdery lipase preparation were freeze dried, to each of which 5 mL of solvent n-hexane, t-butanol or acetone was added. With 0.163 g of glycerin and 0.5 g of oleic acid further added together with 0.5 g of molecular sieves 3A (supplier: Wako pure chemical Industries) as dehydrating agent, the mixture was shaken 48 hr at 37° C for a reaction under dehydration.

For activity measurements, Lipases PL-266 and PL-679 were assayed by a Kokusho et al.'s method (Agric. Biol. Chem. 45(5), 1159 (1982)), Lipase AL by another Kokusho et al.'s method (yukagaku 23(2), 98 (1974)), Lipase PS by Watanabe et al.'s method (Argic. Biol. Chem. 41, 1353 (1977)), and other lipases by Fukumoto et al.'s method (J. Gen. Appl. Microbiol. 9, 353 (1963)) except for the Mucor miehei lipase from NOVO, for which the nominal lipase activity data presented by the company was used as it was.

The amount of free fatty acid was determined by alkalimetry to estimate the amount of fatty acid consumed for esterification, which was compared to the added amount of fatty acid to calculate the percentage decrease of fatty acid. To measure the moisture content of the reaction solution, a moisture measuring meter Mitsubishi Chemical Industries Model CA-05 was used for coulometric titration (Karl Fischer method). Table 2 is the results.

TABLE 2

| | Percentage decrease of fatty acid by reaction in | | |
|---|---|---|---|
| Lipase | n-Hexane (50 ppm H$_2$O) | t-Butanol (100 ppm H$_2$O) | Acetone (200 ppm H$_2$O) |
| Lipase PL-679 | 94.6 | 94.0 | 48.0 |
| Lipase PL-266 | 94.3 | 82.0 | 43.0 |
| Lipase AL | 82.5 | 80.0 | 40.0 |
| Lipase PS | 67.2 | 26.5 | 11.1 |
| Talipase | 0 | 0 | 0 |
| Lipase AP | 0 | 0 | 0 |
| Mucor miehei lipase (NOVO sp 225) | 7.9 | 0 | 0 |

Table 2 shows that the alkaline high molecular weight lipases unambiguously presented satisfactorily high activities in trace water environment while the low molecular weight lipases have no or almost no activities in this condition.

Accordingly, any alkaline high molecular weight lipase from microbial source other than the ones listed herein could be used in the invention without any restriction on the source and species thereof as long as the enzyme concerned has a molecular weight of 100,000 or more and exhibits high activities in the esterification as mentioned above.

In the invention, an alkaline high molecular weight lipase may be used either in the form of purified preparation or crude one, which is immobilized and, if necessary, dried before application. The ion exchange resin that can be used as the carrier of the immobilized enzyme is a weakly basic ion exchange resin based on polymethacrylate. Examples are DEAE-Toyopearl (Supplier:Toso Co., Ltd.), Sepabeads (Mitsubishi Chemical), etc. Among these, DEAE-Toyopearl 650 whose grain size is between 50 and 150 μm is particularly preferable for use.

For immobilization, the resin as mentioned above is added to a culture broth or aqueous solution of either crude enzyme or enzyme preparation partially purified by solvent fractionation, salting with ammonium sulfate and/or the like or further purified by purifying means, for example, by a treatment on ion exchange resin, gel filtration, and/or ultrafiltration. After agitation for a duration of time long enough for the carrier to adsorb the enzyme, the solution is centrifuged and filtered to recover carrier with the enzyme immobilized thereon.

If an ion adsorbent is used for the support of immobilized enzyme, the enzyme solution is desalted as necessary, for example, by ultrafiltration and adjusted to a proper pH depending on the isoelectric point of the enzyme used before the treatment for adsorption is started for immobilization. In case of the above examples of alkaline high molecular weight lipase, for exam- It is noted that because of faster reaction and no large equipment requirement, the continuous process of the invention is very advantageous from economical viewpoint.

Other objects, features and advantages of the invention will appear more fully from the following detailed description thereof taken in connection with the accompanying drawings.

DESCRIPTION OF THE PREFERRED EMBODIMENTS

In the process of interesterification embodying the invention, natural or processed oil or fat of vegetable or animal origin, or fractional component of such oil or fat separated by fractionation, or mixed oil or fat of similar nature may be used for the raw material glycerides.

Examples of applicable oils and fats are soybean oil, cotton seed oil, rapeseed oil, olive oil, corn oil, coconut oil, safflower oil, sunflower oil, camellia oil, sasanqua oil, palm kernel oil, palm oil, palm oil mid-fraction, sal oil, illipe fat, furuwarah fat, shea fat, mowrah oil, phulwara fat, Borneo tallow, beef tallow, lard, milk fat, fish oil, as well as fractionated products and processed oils and fats prepared from the above. Further examples are dilaurin, dipalmitin, diolein, distearin, trilaurin, tripalmitin, triolein, tristearin, etc. For a reaction to produce symmetrically interesterified oil or fat, the higher the proportion of glycerides that have the same fatty acid residue at the 2-position is, the more preferable the raw material oil or fat is.

Saturated or unsaturated fatty acids having 4 to 22 carbon atoms can be used for the interesterification of the invention. Examples of these fatty acids are butyric acid, caproic acid, caprylic acid, capric acid, lauric acid, myristic acid, palmitic acid, stearic acid, oleic acid, linolic acid, ricinoleic acid, arachidonic acid, eicosapentaenoic acid, etc. Instead of the above fatty acids, the corresponding esters with alcohols having up to 20 carbon atoms, preferably up to 4 carbon atoms may be used. Preferable examples of such alcohols are methanol, ethanol, 1-propanol, 1-butanol, etc.

These raw materials may be refined as necessary before use. Alternatively, upstream of the reactor column, a refining column packed with an oil and fat refining agent, for example, a proper ion exchange resin, activated carbon, activated clay, acid clay, alumina or the like may be disposed so oil or fat may be refined by passage across the precolumn before entering the reactor column. Through such refining, the service life of the enzyme can be prolonged and the reaction yield be improved.

The above oils or fats and fatty acids or esters may be used in any combination, no restriction being imposed on the selection and combination of these materials.

Only the alkaline high molecular weight lipase is effectively applied as the enzyme catalyzing the reaction of the invention, while the conventional low molecular weight acid or neutral lipase is hardly effective. It is noted that with such conventional lipase the continuous process of interesterification of the invention that occurs in presence of trace water proceeds almost nothing. In the invention, any of alkaline high molecular weight lipases from microbial sources that have the 1,3-positional specificity may arbitrarily be selected for use. Examples of such lipases are *Alcaligenes, Achromobacter* and *Pseudomonas* lipases.

Actual examples of the applicable enzyme are Lipase PL-266 (Japanese Patent Publication 58-36953) produced by *Alcaligenes sp.* PL-266 (Fermentation Research Institute Stock No. 3187), Lipase PL-679 (Japanese Patent Publication 60-15312) produced by *Alcaligenes sp.* PL-679 (Fermentation Research Institute Stock No. 3783. The same is deposited at American Type Culture Collection, U.S.A. under the deposit number ATCC 31371 and also deposited in German Collection of Nicoorganisms, Germany under the deposit number DSM 1239.), Lipase AL (Japanese Patent Publication 49-32080) produced by *Achromobacter sp.* AL-865 (Fermentation Research Institute Stock No. 1213) and Lipase PS (Japanese Patent Publication 56-28516) produced by *Pseudomonas nitroreducens* var. thermotolerans (Fermentation Research Institute Stock No. 1338). These are effective lipases that satisfactorily catalyze the interesterification with a positional specificity particularly in presence of trace water, condition in which lipases as proposed by prior art cannot induce the interesterification. It is noted that all of these effective lipases are extracellular enzymes.

Table 1 compares examples of lipases of prior art and examples of the lipase applicable to the invention in the molecular weight and optimum pH. Lipases PL-266, PL-679, AL and PS given in the table are all alkaline high molecular weight lipases whose optimum pH and molecular weight are higher than 8.0 and 100,000, respectively.

Enzymes having the monomolecular protein structure have molecular weights up to 100,000, mostly between 10,000 and 50,000, while larger enzymes having molecular weights not lower than 100,000 either have the subunit structure with or without glycoprotein or lipoprotein binding. Lipases from bacterial sources sometimes belong to the latter type. These lipases having molecular weights of 100,000 or more are called high molecular weight lipase herein to differentiate from low molecular weight lipases whose molecular weight is lower than 100,000 and which are different in the catalytic performance in interesterification. It is found from Table 1 that according to the above classification of lipases by molecular weight, high molecular weight lipases are characterized by optimum pHs higher than 8.0 while low molecular weight lipases have pH values lower than 8.0.

It is noted that the above classification of lipases by molecular weight assumes the molecular weight determination by fractionation on a column of Sephadex G200 (Pharmacia) followed by comparison of the obtained data to the calibration curve made by use of bovine serum albumin of molecular weight 68,000, rabbit muscle aldolase of molecular weight 158,000 and bovine liver catalase of molecular weight 240,000 as reference proteins.

TABLE 1

| Lipase (source) | M.W. ($\times 10^3$) | Opt. pH | References |
|---|---|---|---|
| Prior art: | | | |
| *Rhizopus delemar* | 41.0–44.0 | 5.6 | |
| *Aspergillus niger* | 38.0 | 5.6 | yukagaku 13(10) 136 (1982) | ple, 1 g of the resin can adsorb up to 100,000 to 300,000 U/g (hydrolytic activity units) of the enzyme after 10 to 60 minutes agitation at pH 6 to 11, capable of removing at least 80 to 90% of the lipase activity from the lipase solution.

Beside immobilization as mentioned above, the enzyme material may be used as it is or the enzyme may be fixed with some proper diluent and binder. Examples of the above diluent and binder are proteins like lacto albumin, soybean proteins and wheat proteins, saccharides like lactose, sucrose, starch, chitosan and cellulose acetate, clay minerals like bentonite and celite, etc. For fixing with the above diluent and binder, a mixture of a powdery enzyme and diluent and binder materials is mixed with a small volume of water or organic solvent for molding.

The isolated immobilized enzyme or fixed enzyme as mentioned above is dried to a moisture content of preferably 5% or under, more preferably 2% or under and most preferably about 1% or under before use. Applicable methods of drying are drying in air under heating, immersion in dry organic solvent for dehydration followed by solvent evaporation, freeze drying or a combination thereof. Among others, freeze drying is preferable as such method.

In this invention, though the preferable moisture content of enzyme preparation is specified to be 5% or under, this does not mean that the enzyme preparation with a higher moisture content fails to catalyze the intended reaction of interesterification. Namely, to pass the substrate solution across a reactor column charged with lipase in continuous process, actually, it is necessary to apply a pressure of several kilograms to ten-odd kilograms per square centimeters. Under the above pressure, even if the lipase preparation initially contains a high moisture content, excess moisture will be soon physically squeezed from the enzyme preparation until the moisture content thereof reduces, for example, to about 10%. Further, as oil or fat starts running as the substrate containing just trace water as specified herein, enzymatic hydrolysis of the substrate consumes excess water that presents in the enzyme preparation, reducing the moisture content thereof down to 5% or under after a lapse of certain time. Further the contact of the enzyme preparation to the substrate or substrate solution containing just trace moisture in a long continuous process reduces the moisture content of the enzyme preparation until such moisture content reaches the equilibrium level of about 1 to 2%. It is noted that when a substrate dissolved in n-hexane was continuously passed across a column packed with a DEAE-Toyopearl immobilized lipase preparation particularly containing 0.1 to 5.0% moisture, the column pressure was found to stay below 1 kg/cm².

Notwithstanding the above, it is not preferable to start the reaction with the initial moisture content of the enzyme preparation over 5%, since it then takes too much time to attain the equilibrium level of moisture content and during that time there occurs hydrolysis more than necessary leading to abundant production of undesirable diglycerides that reduce the yield of interesterified oil or fat. This point will be illustrated in Experiment 2.

A higher moisture content of the enzyme preparation has another problem that since there appears a higher resistance to the substrate flow across the reactor column, it becomes difficult to achieve a flow rate sufficiently high for the efficient reaction.

Experiment 2

2.5 g of freeze dried DEAE-Toyopearl immobilized Lipase PL-679 preparation (15,000 U/g support) was allowed to soak 25 mg of distilled water (corresponding to 1% of the weight of the immobilized enzyme preparation) and then suspended in 50 mL of n-hexane. The suspension was poured in a jacketed 150 mm long column 10 mm across in inside diameter for packing.

The same procedure was repeated except that the soaked quantity of distilled water was changed to 0, 50, 100, 138 and 250 mg (corresponding to 0, 2, 4, 5.5 and 10%, respectively, of the weight of the immobilized enzyme preparation) to prepare immobilized enzyme columns different from one another in moisture content.

354.4 g of palm oil mid-fraction (POMF) and 283.6 g of stearic acid were dissolved with 0.4 mL of distilled water in 1,600 g of n-hexane. The solution was passed across a jacketed 150 mm long column 10 mm across in inside diameter that was packed with 6 g of granulated celite containing 2 g of soaked distilled water to adjust the moisture content of the substrate solution to 700 ppm.

The above immobilized enzyme columns different from one another only in the moisture content was fed from below with the substrate solution at a flow rate of 5.5 mL/hr while keeping the reaction system at 45° C. Reaction solutions that came out of the individual immobilized enzyme columns were analyzed by methods as mentioned hereinafter in Example 1 for the moisture content, fatty acid composition of triglycerides and glyceride composition. Table 3 is the results.

TABLE 3

Effect of the water addition to the immobilized enzyme preparation on interesterification

| Water (%) added to immobilized enzyme | Days | Stearic acid (%) in triglycerides | Triglycerides (%) in glyceride composition | Moisture content (ppm) of column output |
|---|---|---|---|---|
| 0 | 1 | 35.3 | 91.0 | 190 |
|  | 3 | 35.2 | 86.0 | 210 |
|  | 5 | 34.4 | 89.1 | 200 |
| 1 | 1 | 35.0 | 89.6 | 230 |
|  | 3 | 34.3 | 87.5 | 210 |
|  | 5 | 34.4 | 88.2 | 210 |
| 2 | 1 | 34.8 | 82.1 | 330 |
|  | 3 | 34.7 | 85.8 | 190 |
|  | 5 | 32.8 | 87.2 | 210 |
| 4 | 1 | 34.7 | 78.4 | 460 |
|  | 3 | 34.5 | 78.8 | 380 |
|  | 5 | 34.4 | 80.4 | 210 |
| 5.5 | 1 | 34.5 | 75.3 | 450 |
|  | 3 | 34.4 | 75.5 | 440 |
|  | 5 | 33.8 | 76.0 | 380 |
| 10 | 1 | 32.5 | 70.2 | Separation of water droplets |
|  | 3 | 33.6 | 71.3 | 460 |
|  | 5 | 33.2 | 75.1 | 400 |

Note:
The raw material palm oil mid-fraction (POMF) contained 3.6% stearic acid before reaction.

Table 3 shows that if water is added over 5% to the immobilized enzyme preparation the proportion of triglycerides decreases in the glyceride composition of reaction product. This means a lower yield of the target interesterified oil or fat. It is also found that 10% water exceeds the moisture holding capacity of the immobilized enzyme preparation, so excess water separates to be released into the reaction solution.

Being active in the trace water environment, the enzyme used in this invention stands stable use particularly in organic solvents, so an organic solvent can be added as necessary to the reaction system.

For this purpose, any organic solvent is applicable that is liquid at the reaction temperature, dissolves the substrate satisfactorily and yet does not disturb the interesterification. Examples of such organic solvent are aliphatic hydrocarbons, like n-hexane, isooctane, n-heptane, n-pentane and petroleum ether, tertiary butyl alcohol, acetone, etc. Particularly, the aliphatic hydrocarbon, for example, n-hexane is preferable. These solvents may be used independently or in combination. In this invention, the interesterification can be induced in conditions as described below.

Namely, in the invention, the substrate oil or fat is interesterified in presence of a fatty acid, fatty acid ester or different oil or fat, which may present in any arbitrary molar ratio to the substrate oil or fat that satisfies the particular purpose of the reaction. There is no particular restriction in this regard. Further, the above combination may contain three or more reactant materials as necessary for the reaction.

The immobilized alkaline high molecular weight lipase preparation preferably has a higher specific activity for more efficient reaction. Thus, the lipase preparation has an activity of preferably 3,000 to 300,000 U/g and practically of 10,000 to 100,000 U/g.

To pack the reactor column, the enzyme preparation is suspended in the reaction solvent or oil or fat and poured into the column using a caution to avoid formation of any air bubbles. In the continuous process of interesterification, the feeding rate of the substrate can be adjusted depending on the charged quantity of the enzyme preparation, so there is no particular restriction on such charged quantity of enzyme. An organic solvent, if used, can be added 10 to 90% w/w, preferably 20 to 80% w/w to the reaction system.

The substrate solution that is continuously fed to the reactor column must be preadjusted to a moisture content between 100 and 1800 ppm, preferably between 100 and 1500 ppm, and more preferably between 200 and 1000 ppm.

To adjust the moisture content of the substrate solution, the necessary amount of water may be added to the substrate solution or the superfluous amount of water be removed by dehumidification.

To increase the moisture content, for example, the necessary amount of water may be calculated and added directly. Since only a very small amount of water is necessary, however, easier adjustments are to bubble the substrate solution with steam, humidifying air or the like or pass the solution across a precolumn packed with hygroscopic solid that is moistened beforehand.

For dehumidification, the substrate solution can be bubbled, for example, with dry inert gas such as nitrogen to effect adjustments. Alternatively, part of the substrate solution can be passed across a precolumn packed with a dehydrating agent, for example, molecular sieves.

Further, if the moisture saturation level of the substrate solution is too low to achieve a desirable moisture content, a change in the substrate concentration of the solution or a change in the solvent composition by addition of a hydrophilic solvent, such as acetone, methanol, ethanol or t-butanol, will solve the problem.

Anyway, normally, the substrate solution used in this invention contains moisture at the level of 10-100 ppm.

Therefore, what is needed is only to adjust total moisture content in the substrate solution to the range of the claim.

The reaction solution output from the reactor column for the continuous process has a moisture content in a range from 50 to 800 ppm, which is always lower than the moisture content of the substrate solution that is input to the column because of consumption of a very small amount of water for interesterification. If the moisture content of input substrate solution is adjusted according to the target interesterified oil or fat product and in consideration of the flow rate of substrate solution, the interesterification is achieved with the moisture content of the output reaction solution almost automatically satisfying the above requirement. This point is illustrated in the next experiment.

Experiment 3

2.5 g of freeze dried DEAE-Toyopearl immobilized Lipase PL-679 preparation (100,000 U/g carrier) was suspended in 50 mL of n-hexane and poured in a 150 mm long column 10 mm across in inside diameter for packing.

354.4 g of P O M F and 283.6 g of stearic acid were dissolved in a mixed solvent of 1440 g of n-hexane and 193 g of acetone. The above substrate solution was found to contain 90 ppm moisture. The immobilized enzyme column was fed from below with the above substrate solution at a flow rate of 27.5 mL/hr. The reaction solution output from the column was sampled and analyzed by a Karl Fischer type moisture measuring meter for the moisture content (Mitsubishi Chemical Industry's Model CA05), Iatroscan, and gas chromatography (according to analytical methods as described later in Example 1) for glyceride composition, fatty acid composition of triglycerides, respectively. It is noted that the reaction system was kept at 45° C.

Further, to substrate solutions of the same composition, 0.14, 0.36, 1.04, 1.50, 1.95, 2.75, 3.32, 3.66 and 4.79 mL of distilled water were added independently to prepare substrate solutions containing 150, 250, 550, 750, 950, 1300, 1550, 1700 and 2240 ppm moisture. Beside, 354.4 g of P O M F and 283.6 g of stearic acid were dissolved in 1589 g of n-hexane and 16.8 mL of ethanol and 0.43 g of distilled water were added to the mixture to prepare a substrate solution containing 280 ppm moisture.

Each of the above substrate solutions was passed across an immobilized enzyme column as prepared above. All the reaction solutions were analyzed for the moisture content, glyceride composition, and fatty acid composition of triglycerides. Table 4 is the results.

TABLE 4

| Enzyme | Moist. content of substrate solution (ppm) | Stearic acid (%) in triglycerides | Triglycerides (%) in glyceride composition | Moist. content (ppm) of column output |
|---|---|---|---|---|
| Lipase PL-679 | 90 | 5.8 | 95.1 | 40 |
| | 150 | 19.8 | 94.4 | 70 |
| | 250 | 28.9 | 93.5 | 120 |
| | 550 | 29.3 | 92.1 | 170 |
| | 750 | 29.2 | 90.6 | 210 |
| | 950 | 30.8 | 90.0 | 460 |
| | 1300 | 29.9 | 87.8 | 600 |
| | 1550 | 30.3 | 85.1 | 640 |
| | 1700 | 29.7 | 84.5 | 750 |
| | 2240 | 31.1 | 78.6 | 830 |

TABLE 4-continued

| Enzyme | Moist. content of substrate solution (ppm) | Stearic acid (%) in tri- glycerides | Triglycerides (%) in glyceride composition | Moist. content (ppm) of column output |
|---|---|---|---|---|
| | 280* | 29.4 | 84.4 | 770 |

Note:
Above data refers to analyses made 4 days after the start of the reaction. In case of the asterisked data, the moisture adjustment was made with addition of 0.6 w/w ethanol instead of 8.5% w/w acetone.

2 mL of *Rhizopus delemar* lipase suspension (Boehringer, 50,000 U/mL) was dialyzed against distilled water. The dialyzed solution was diluted with 10 mL of distilled water and then allowed to be adsorbed by 10 g of CELITE. The CELITE was then freeze dried in vacuum to remove moisture to give an immobilized lipase preparation. A suspension of 10 g of the above immobilized enzyme preparation in 50 mL of n-hexane was poured in a 150 mm long column 10 mm across in inside diameter for packing. Two substrate solutions having 750 and 2800 ppm moisture, respectively, prepared according to the method as mentioned above were fed to individual immobilized enzyme columns from below at a rate of 27.5 mL/hr and the output reaction solution was analyzed by the methods as mentioned later in Example 1 for the moisture content, glyceride composition and fatty acid composition of triglycerides. Table 5 includes the results.

Further, 2.5 g of Lipase 3A (NOVO, Mucor miehei sp 225 lipase immobilized on Duolite S761) was freeze dried in vacuum and suspended in 50 mL of n-hexane for use in packing two reactor columns as in the preceding paragraph. Two substrate solutions (containing 750 and 2800 ppm moisture, respectively) were fed to individual columns from below at a flow rate of 27.5 mL/hr. The reaction solutions output from the individual columns were sampled and similarly analyzed for the moisture content, glycride composition and fatty acid composition of triglycerides. Table 5 includes the results.

TABLE 5

| Enzyme | Moist. content of substrate solution (ppm) | Stearic acid (%) in tri- glycerides | Triglycerides (%) in glyceride composition | Moist. content (ppm) of column output |
|---|---|---|---|---|
| Rhizopus lipase | 750 | 5.1 | 87.1 | 200 |
| | 2,800 | 18.6 | 72.1 | 1,700 |
| Mucor lipase | 750 | 4.8 | 86.8 | 180 |
| | 2,800 | 15.4 | 71.4 | 1,710 |

Note:
Above data refers to analyses made 4 days after the start of the reaction.

Table 4 shows that in a condition that a substrate solution containing less than about 100 ppm moisture was fed to the reactor column and a reaction solution containing less than 50 ppm moisture was output therefrom the interesterification hardly occurred as evidenced by the small percentage of stearic acid composition of triglycerides accounted for by stearic acid. By contrast, in a condition that a substrate solution containing moisture between 100 and 1800 ppm was fed and a reaction solution containing moisture between 50 and 800 ppm was output the interesterification proceeded smoothly giving triglycerides at a high yield. In a condition that a substrate solution containing more than 1800 ppm moisture was fed and a reaction solution containing more than 800 ppm moisture was output, however, triglycerides were produced at a lower yield. By contrast, it is found from Table 5 that in case of *Rhizopus* or *Mucor* lipase the interesterification did not occur fully when the substrate solution contained up to 2800 ppm moisture, indicating that a further increase in the moisture content of substrate solution was necessary.

It is desirable to select a proper reaction temperature in consideration of the substrate material, boiling point of the solvent, enzyme species, etc. Normally, the reaction proceeds at a temperature below 80° C., preferably in a range from 30° to 70° C. Excessively high reaction temperatures are rather unpreferable since reaction intermediates 1,2-diglycerides get liable to fatty acid rearrangements at 2-position.

The time during which the substrate must be retained in the reactor column for the effective reaction is not particularly limited since this parameter is determined depending on the target percentage interesterification. For example, to introduce stearic acid in glyceride molecules of P O M F as illustrated later in Example 5, a retention time of about 7 or 26 minutes is long enough to give a percentage interesterification of 67% or 94%, respectively.

The alkaline high molecular weight lipase as used in this invention can stably and efficiently catalyze interesterification for a long time, so once packed with the preparation of the above enzyme, the reactor column can stand prolonged use. For example, in Example 5 as mentioned later where P O M F was reacted with stearic acid for transesterification at a reaction temperature of 45° C. in presence of DEAE-Toyopearl immobilized Lipase PL-679 preparation with the moisture content of the substrate solution set to 700 ppm, the immobilized enzyme preparation was found to have a half life of about 190 days. Assuming 67% for the percentage interesterification, this means that about 20 tons of raw material glyceride oil could be processed per kilogram of the immobilized enzyme for two half lives.

In the next experiment, the continuous process of interesterification embodying the invention is compared to the batch process of interesterification as disclosed in Japanese Patent Application 62-45302 in the efficiency of reaction.

Experiment 4

2.5 g of DEAE-Toyopearl immobilized Lipase PL-679 preparation freeze dried in vacuum (20,000 U/g) was suspended in 50 mL of n-hexane and poured in a jacketed 150 mm long column 10 mm across in inside diameter for packing. Another jacketed 150 mm long column of 10 mm across in inside diameter was packed with 6 g of Celite soaked with 2 mL of distilled water to provide a precolumn for use to adjust the moisture content of substrate solution.

354.4 g of P O M F and 283.6 g of stearic acid were dissolved in 1600 g of n-hexane. After addition of 5 mL of distilled water, the solution was agitated and then left 30 minutes to get supernatant, which was used as the substrate solution containing 200 ppm moisture.

The above substrate solution was fed by a micropump to the precolumn from below at a flow rate of 170 mL/hr to adjust the moisture content of substrate solution to 700 ppm. After passage across the precolumn, the substrate solution was continuously fed 10 days to the immobilized enzyme column from below at a flow rate of 24.0 mL/hr (37° C.) for the reaction. The reaction solution output from the reactor column during this period was analyzed by the same methods as mentioned in Example 1. There was produced about 6.4 kg of interesterified glyceride oil at a percentage interesterification of 95%.

By contrast, in a batch process of interesterification as proposed in Example 3 of Japanese Patent Application 62-45302, about 0.66 kg of interesterified glyceride oil was produced at interesterification rate of 95% in a 10 day operation. This means that the continuous process of the invention is about 1.8 times as efficient as the above batch process when compared on enzyme unit basis.

In the present invention, to recover the interesterified oil or fat from the reaction solution that is output from the reactor column, the reaction solution as it is or with addition of a solvent, for example, hexane, acetone, ethanol or the like can be cooled below the melting point of the target interesterified oil or fat for precipitation thereof, precipitated oil or fat being recovered by a centrifuge or filtration. The above method is also applicable to the removal of undesirable oil, fat and/or fatty acids from the reaction solution. It is also possible to add an alcoholic or aqueous solution of ammonia, caustic soda, calcium hydroxide, or the like to the reaction solution so undesirable free fatty acids may be removed as soap.

It is noted that before application of the above method of recovery of interesterified oil or fat, the reaction solution can be distilled or filtered across a membrane filter to remove the reaction solvent for recovery of the solvent-free oil or fat fraction, which is redissolved in a solvent, such as n-hexane, acetone, ethanol, propanol or t-butanol, or a mixture of two or more of these solvents. The target interesterified oil or fat can then be isolated for recovery as mentioned in the preceding paragraph. Alternatively, after the above solvent removal, the residue that is left can be distilled to separate free fatty acids from oil or fat. The oil or fat is then redissolved in a solvent, such as acetone, n-hexane, ethanol, or the like, as mentioned above, for solvent fractionation, precipitation, etc. for further refining.

Interesterified oil or fat products thus prepared will find applications in industries as related to food processing, cosmetics, medicines, agricultural chemicals, paints, printing, etc.

An effect of the invention is thus efficient production of interesterified oils and fats at high yield by continuous process wherein the substrate oil or fat is interesterified in trace water environment in presence of a fatty acid, fatty acid ester or different oil or fat under direct action of alkaline high molecular weight lipase. A merit of such continuous process of interesterification is that since the reaction system requires only trace water no moisture content control mechanism is necessary for moisture content adjustments by dehydration during the reaction while with the undesirable hydrolysis suppressed, side products diglycerides that lower the yield of the interesterified oil or fat are produced almost nothing. Since no moisture content adjustment is necessary during the reaction, treatments for water addition and dehydration that may cause inactivation of the enzyme can be avoided, so the enzyme stands prolonged use. Further, the process of the invention proceeds at a fast reaction rate and requires no large equipment, so the process provides a method of high economical merit that can be suitably applied to the production of interesterified oils and fats at the industrial scale.

Thus, in the invention, cheap oils and fats can be readily and profitably upgraded to convert to expensive interesterified oils and fats of high added value by a continuous process in simple reaction conditions. For example, the process can be applied to modification of various edible oils and fats, for example, conversion of cheap palm oil to an expensive cacao butter substitute.

Immobilized lipase preparations as used in Examples of the invention were prepared by the following methods:

How to Prepare Immobilized Lipase Preparations - Method 1

*Alcaligenes sp.* PL-679 bacteria were grown by a method as disclosed in Japanese Patent Publication 60-15312 to get 15 L of culture, which was spun 10 minutes at 10,000×g on centrifuge. 450 g of bentonite was added to the supernatant and the mixture was agitated 1 hr while cooling and then spun on centrifuge to recover bentonite that had adsorbed Lipase PL-679. By adding 10 L of 1% polyethylene glycol 4000 solution to the bentonite, the enzyme Lipase PL-679 was extracted from bentonite. Removal of bentonite by centrifugation gave 10 L of bentonite-free Lipase PL-679 solution.

100 g (on dry weight basis) of DEAE-Toyopearl (Toso Co., Ltd.) was immersed 4 hours in 5 L of aqueous 1N NaOH solution. By filtration under suction, DEAE-Toyopearl was recovered on filter paper No. 1. DEAE-Toyopearl on filter paper was washed with distilled water until the pH of filtrate lowered to 8.0. DEAE-Toyopearl was thus activated.

10 L of the above bentonite free Lipase PL-679 solution was agitated 1 hour at 4° C. with the above activated DEAE-Toyopearl to allow the latter to adsorb the enzyme for immobilization. After washing with water for removal of polyethylene glycol 4000 and filtration under suction, a DEAE-Toyopearl immobilized Lipase PL-679 preparation was recovered on filter paper No. 1. The immobilized enzyme preparation was freeze dried 48 hours. A dry DEAE-Toyopearl immobilized Lipase PL-679 preparation was thus prepared for use in Examples that follow.

It is noted that the above immobilized enzyme preparation had an activity of 100,000 U/g support. Further, the same procedure as above was repeated except for use of 500 g of DEAE-Toyopearl to get another preparation of dry DEAE-Toyopearl immobilized Lipase PL-679 preparation (20,000 U/g carrier).

Further, *Alcaligenes sp.* PL-266 bacteria was grown by a method as disclosed in Japanese Patent Publication 58-36953 to get 15 L of culture. Applying the same method as mentioned above, a DEAE-Toyopearl immobilized Lipase PL-266 preparation was prepared from the above culture, which had an activity of 10,000 U/g carrier.

Further, *Achromobacter sp.* AL-865 bacteria was grown by a method as disclosed in Japanese Patent Publication 49-32080 to get 15 L of culture, from which DEAE-Toyopearl immobilized Lipase AL preparation was prepared by the same method as applied above. This enzyme preparation had an activity of 10,000 U/g.

Further, 5 g of Lipase PS powder (Sapporo Breweries, 16,000 U/g carrier) was dissolved in 500 mL of water and the solution was spun on centrifuge to get supernatant, to which 15 g of bentonite was added. With the extracted enzyme, the above method for enzyme immobilization were repeated at a reduced scale of 1/30 to get a DEAE-Toyopearl immobilized Lipase PS preparation, which had an activity of 10,000 U/g.

How to Prepare Immobilized Lipase Preparations - Method 2

*Alcaligenes sp.* PL-679 bacteria was grown by a method as disclosed in Japanese Patent Publication 60-15312 to get 15 L of culture, which was processed by the same method of enzyme immobilization as applied to Method 1 to get 10 L of bentonite-free Lipase PL-679 solution. To this lipase solution, 3 L of DEAE-cellulose fully equilibrated in 0.01M phosphate buffer of pH 9.0 was added for adsorption of the enzyme. After washing with the same buffer for removal of polyethylene glycol, 5 L of 0.2M NaCl solution was added to dissolve Lipase PL-679 from DEAE-cellulose. After filtering out DEAE-cellulose, the enzyme solution was ultrafiltered to 10 times in concentration and then desalted to a salt content of 1% or under. 500 mL of purified Lipase PL-679 solution was thus produced.

1 hour agitation of 50 mL of the above purified lipase solution at 4° C. with 50 g of Prolacto derived from lacto albumin (supplier: Toyo Jozo) followed by 48 hours freeze drying gave 50 g of dry Prolacto immobilized Lipase PL-679 preparation, which had an activity of 10,000 U/g.

Further, 1 hour agitation of 50 mL of the above purified Lipase PL-679 solution at 4° C. with 50 g of chitosan followed by 48 hours freeze drying gave 50 g of dry chitosan immobilized Lipase PL-679 preparation, which had an activity of 10,000 U/g support.

Furthermore, 9 g of cellulose acetate was dissolved in 100 mL of acetone. The solution was agitated with 1 g of Lipase PL-679 powder and acetone was evaporated under reduced pressure to produce a cellulose acetate immobilized Lipase PL-679 preparation, which had an activity of 10,000 U/g. This enzyme preparation was cut into 1 mm dice for use.

To further illustrate this invention, and not by way of limitation, the following examples are given.

EXAMPLE 1

2.5 g of dry DEAE-Toyopearl immobilized Lipase PL-679 preparation (100,000 U/g support, moisture content: 0.1%) was suspended in 50 mL of n-hexane and a jacketed 150 mm long column 10 mm across in inside diameter was packed with the resultant suspension.

On the other hand, 6 g of granulated CELITE was allowed to soak 2 mL of distilled water and then used to pack another jacketed 150 mm long column 10 mm across in inside diameter for use as the precolumn to adjust the moisture content of substrate solution.

354.4 g of P O M F and 283.6 g of stearic acid were dissolved in 1,600 g of n-hexane and the solution was agitated with 5 mL of distilled water. The solution was left 30 minutes and the supernatant was used as the substrate solution, which contained 200 ppm moisture.

The substrate solution was pumped by a micropump to feed the precolumn from below at a rate of 170 mL/hr or under to adjust the moisture content thereof to 700 ppm.

Figure 1:
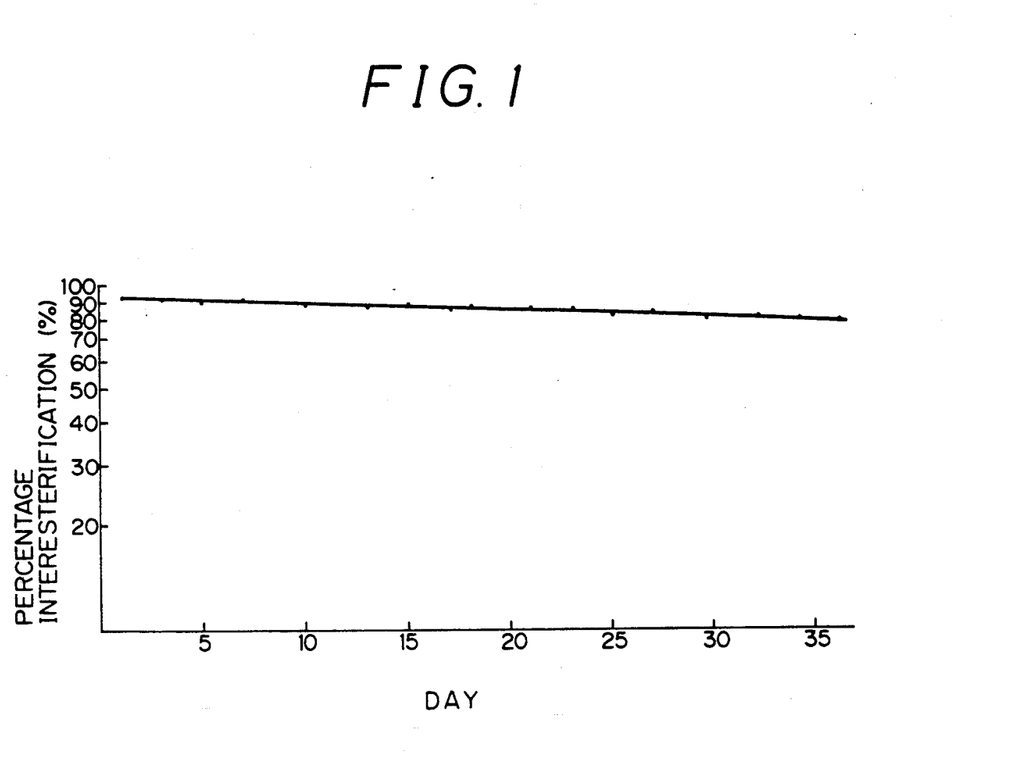
FIG. 1 is the time course of the percentage interesterification as observed in Example 1.

The substrate solution that came out of the precolumn was fed to the column packed with the DEAE-Toyopearl immobilized Lipase PL-679 preparation from below at a rate of 27.5 mL/hr (SV=2.3 hr$^{-1}$). The reaction system was kept at 45° C. While continuously feeding the column for 35 days, the reaction solution was sampled at intervals of 24 hours and analyzed for the proportion of stearic acid ($C_{18:0}$) in triglycerides, the proportion of oleic acid ($C_{18:1}$) at the 2-position of triglycerides, proportion of triglycerides in the glyceride composition, percentage interesterification, and moisture content of the reaction solution output from the reactor column. Table 6 and FIG. 1 are the results.

In the above analyses, the proportion of stearic acid in triglycerids was estimated by the following method. The reaction solution was diluted with a same volume of methylene chloride and 50 μL of the dilution was applied in a band form to a 1 mm thick silica gel plate containing a fluorescent reagent (Merck). After 10 cm development with a mixed solvent of petroleum ether, ether and acetic acid (70 : 30 : 1, v/v), the plate was exposed to the UV light of 254 nm to detect the triglycerides spot, which was scraped off to put into a stoppered test tube. The triglycerides were analyzed for the fatty acid composition in conformity to Sec. 2.4.20.2-77 and Sec. 2.4.21-71 of a book titled "Kijun Yushi Bunseki-ho" (Standard Methods of Fat/Oil Analysis, compiled by Nihon yukagaku Kyokai), namely, sections that described how to prepare methyl ester of fatty acids (boron trifluoride-methanol procedure) and fatty acid composition (gas chromatography), respectively. The fatty acid composition at the 2-position of triglycerides was determined by the following analysis. The above method of triglyceride isolation was repeated at the fivefold scale. The triglyceride spot that was scraped off was put in 50 mL of mixed solvent of chloroform and methanol (2 : 1, v/v) to extract glycerides from silica gel. The extracts was evaporated to dryness and the residue was shaken with 6 mL of 1M Tris hydrochloric acid buffer (pH 8.0) containing 50 units of Lipase PL-679 and 1.5 mL of aqueous 0.1% sodium colate solution, 0.6 mL of aqueous 2.2% calcium chloride solution, for 3 minutes reaction at 40° C. After 2 mL of 6N hydrochloric acid was added to stop the reaction, the oily fraction was extracted with use of 2 mL of ethanol and 10 mL of petroleum ether. The extracted oily fraction was developed on the silica gel plate as mentioned above to separate the monoglyceride fraction, which was scraped off to put into a stoppered test tube. The fatty acid composition of monoglycerides was determined by the same analysis as applied to the fatty acid composition of triglycerides. The glyceride composition of the reaction solution was determined by Iatroscan. Namely, the reaction solution was diluted with 2 volumes of methylene chloride and 0.2 μL of the diluted solution was applied to Chromarod SII and developed 10 cm with a solvent system of benzene, chloroform and acetic acid (50:20:1, v/v). The relative areas of individual peaks were determined by Iatroscan TH10. Moisture contents of the substrate solution and the reaction solution output from the reactor column were determined by a Karl Fischer type moisture measuring meter.

The percentage interesterification achieved by a particular lipase was estimated as follows. From available P O M F's data for the fatty acid composition of triglycerides and the fatty acid composition particularly at the 2-position thereof, the fatty acid composition at the 1,3-positions of triglycerides was estimated according to the following equation:

Fatty acids at 1,3-positions =     (1)
[(Fatty acids of triglycerides) × 3 — Fatty acids at 2-position] ÷ 2.

In consideration of the fatty acid composition of the triglycerides of P O M F, the mean molecular weight of such triglycerides was assumed to be about 840. From this numerical figure, the molar fatty acid composition at the 1,3-positions of triglycerides was estimated and from the molar ratio of $C_{18:0}$ added to the P O M F to such fatty acid composition at 1,3-positions, the fatty acid composition at the 1,3-position of triglycerides to be reached when the reaction was equilibrated was estimated. It is noted that Lipase PL-679 has a high specificity at 1,3-positions, capable of catalyzing interesterification only at the 1,3-position of triglycerides.

94.6% w/w of fatty acid residues occupying the 1,3-positions of triglycerides of P O M F is accounted for by the sum of palmitic acid ($C_{16:0}$), oleic acid ($C_{18:1}$) and linoleic acid ($C_{18:2}$). After the reaction reaches the equilibrium, this percentage decreased to 42.7% w/w. It is noted that the percentage interesterification is estimated from the following equation:

$$\text{Percentage interesterification} = \{[(C_{16:0} + C_{18:1} + C_{18:2})_{substrate} - (C_{16:0} + C_{18:1} + C_{18:2})_{reaction\ solution}] \div [(C_{16:0} + C_{18:1} + C_{18:2})_{substrate} - (C_{16:0} + C_{18:1} + C_{18:2})_{equilibrium}]\} \times 100. \quad (2)$$

TABLE 6

| Days | C18:0 (%) in TG's fatty acid composition | C18:1 (%) at 2-position of TG | TG (%) in glyceride composition | Percentage Interesterification (%) | Moist. content (%) of column output |
|---|---|---|---|---|---|
| 1 | 36.4 | 70.9 | 91.0 | 94 | 190 |
| 3 | 36.5 | 70.1 | 86.0 | 94 | 200 |
| 7 | 33.3 | 70.3 | 89.1 | 93 | 220 |
| 15 | 34.9 | 69.8 | 87.2 | 92 | 200 |
| 21 | 34.3 | 70.8 | 86.7 | 90 | 210 |
| 27 | 32.9 | 70.2 | 88.1 | 88 | 190 |
| 32 | 33.0 | 69.7 | 87.4 | 87 | 190 |
| 34 | 32.6 | 70.0 | 86.5 | 86 | 200 |
| POMF | 3.6 | 73.6 | 96.9 | — | — |

TG: Triglycerides

Table 6 and FIG. 1 show that the DEAE-Toyopearl immobilized Lipase PL-679 preparation can be effectively applied to the continuous process of interesterification to produce interesterified oils and fats. It is noted that the above enzyme preparation had a half life of about 190 days if calculated according to the following equation:

$$\text{Half life (days)} = \ln(2/kd) \quad (3)$$

where $kd$ = [ln(Initital percentage interesterification ÷ Percentage interesterification after $t$ days)] ÷ $t$.

It follows that about 5.7 tons of P O M F can be processed per kg of the immobilized enzyme preparation for two half lives in case of 94% of the percentage interesterification.

EXAMPLE 2

2.5 L of the reaction solution discharged from a DEAE-Toyopearl immobilized Lipase PL-679 column according to the process of Example 1 (substrate solution fed for 0 to 80 hours) was left 12 hours at 20° C. and then centrifuged 5,000×g to get 2.2 L of supernatant. Suspension of the precipitate in 0.5 L of n-hexane was also centrifuged as above to get 0.4 L of supernatant. The two supernatant fractions were joined and left 12 hours at 5° C. and further centrifuged as above to get 2.4 L of supernatant. This supernatant was fully shaken with 0.5 L of 25% ammonia aqueous solution and 2 L of ethanol in a separating funnel and then left 1 hour. After the lower ethanol layer was allowed to drain, 0.5 L of distilled water and 2 L of ethanol were added to the upper layer that remained and the funnel was shaken fully. After being left 1 hour, the upper n-hexane layer was recovered, which was concentrated on a rotary evaporator under a reduced pressure of 20 mmHg at 40° C. Further 1 hour evaporation at 60° C. under a reduced pressure of 5 mmHg removed n-hexane to leave 249 g of oily fraction, which was dissolved in 560 mL of acetone. After being left 24 hours at 5° C., the precipitate that formed was recovered on G4 glass filter by filtration under suction. 194 g of the above precipitate was dissolved in 480 mL of acetone and the solution was left 24 hours at 5° C. The precipitate that formed was recovered on G4 glass filter by filtration under suction. 127 g of the precipitate was dissolved in 300 mL of acetone and left 24 hours at 5° C. The precipitate that formed was recovered on G4 glass filter by filtration under suction. The precipitate was treated 24 hours under a reduced pressure of 5 mmHg for evaporation of remaining acetone to get 106 g of product fat. 100 mg of the above fat was dissolved in 0.1 mL of methylene chloride and analyzed by high performance liquid chromatography (HPLC) on an ODS COLUMN (YMC Pack A312, 6×150 mm, supplier: Yamamura Kagaku Kenkyusho). For elution, a mixed solvent of acetonitrile, tetrahydrofuran and methylene chloride (20:8:1, v/v) was passed at a flow rate of 2 mL/min, while detecting peaks of individual fat components with a RI detector (Waters R401). A commercially available cacao butter product was also analyzed by the same methods. Table 7 is the results.

TABLE 7

| | Composition - peak area (%) | | | | |
|---|---|---|---|---|---|
| | DGs | TG molecular species | | | |
| | | POP | POS | SOS | Others |
| Interesterified & fractionated fat | 4.3 | 11.8 | 40.7 | 27.1 | 16.1 |
| Commercially available cacao butter | 4.4 | 15.0 | 37.3 | 26.0 | 17.3 |

Note:
DGs: diglycerides, TG: triglyceride, P: palmitic acid, O: oleic acid, S: stearic acid.

Table 7 shows that P O M F, when upgraded by interesterification followed by cooling, removal of free acids as ammonia salts and fractionation in this order, resembles cacao butter very much in the composition of trigylcerides.

EXAMPLE 3

50 mL of the reaction solution discharged from a DEAE-Toyopearl immobilized Lipase PL-679 column according to the process of Example 1 was evaporated 1 hour at 60° C. on a rotary evaporator under a reduced pressure of 50 mmHg to remove n-hexane, leaving 9 g of oily fraction. 8.5 g of the above fraction was taken in a 20 mL distillation flask to undergo vacuum distillation to distill free fatty acids by heating the flask 20 minutes on oil bath of 240° C. with the inside pressure kept reduced at 3 mmHg by pumping while bubbling with very small quantity of $N_2$ gas. After distillation, the residue was immediately cooled with water to get 4.3 g of oily fraction, which was analyzed by the same methods as applied in Example 1 for the glyceride composition, fatty acid composition of triglycerides and fatty acid composition at the 2-position of triglycerides. Table 8 is the results.

TABLE 8

| | | | Fatty acid removal by distillation | | | | | | | |
|---|---|---|---|---|---|---|---|---|---|---|
| | Glyceride composition (%) | | | Fatty acid composition of TG (%) | | | | Fatty acid composition (%) at 2-position of TG | | |
| | TG | DG | FFA | C16:0 | C18:0 | C18:1 | C18:2 | C16:0 | C18:0 | C18:1 | C18:2 |
| Before distillation | 50.7 | 4.8 | 44.5 | 23.0 | 29.1 | 37.9 | 9.2 | 6.7 | 2.0 | 70.0 | 20.5 |
| After distillation | 90.9 | 6.0 | 3.2 | 21.7 | 31.6 | 37.0 | 8.2 | 8.1 | 6.5 | 66.8 | 17.2 |

Note:
TG: triglycerides, DG: diglycerides, FFA: free fatty acids.

Table 8 shows that free fatty acids can be removed by distillation almost without any rearrangements of fatty acid residues.

Next, 40 g of the oily fraction produced by distillation as above was dissolved in 90 mL of acetone and the solution was left 24 hours at 5° C. The precipitate that formed was recovered on G4 glass filter and redissolved in 90 mL of acetone to repeat the same operation 3 times in total. Finally, evaporation of acetone under a reduced pressure of 5 mmHg at room temperature gave 15.5 g of fat, which was analyzed by high-performance liquid chromatography (HPLC) under the same conditions as mentioned in Example 2. Table 9 is the results.

| | Composition - peak area (%) | | | | | |
|---|---|---|---|---|---|---|
| | DGs | FFA | TG species | | | |
| | | | POP | POS | SOS | Others |
| Interesterified & fractionated fat | 4.5 | 1.1 | 12.4 | 39.1 | 27.3 | 15.6 |
| Commercially available cacao butter | 4.4 | 0.1 | 15.0 | 37.3 | 26.0 | 17.3 |

Note:
DGs: diglycerides, FFA: free fatty acids, TG: triglyceride, P: palmitic acid, O: oleic acid, S: stearic acid.

Table 9 shows that P O M F, when upgraded by interesterification followed by distillation for free fatty acid removal and fractionation, comes to resemble cocoa butter very much in glyceride composition.

EXAMPLE 4

The same continuous process as in Example 1 was run for 3 days to get 2 L of the reaction solution. After addition of 14.8 g of calcium hydroxide and 400 mL of distilled water, the solution was agitated 12 hours at 40° C. Solid residue that precipitated by centrifugation at 1,000×g was removed and the supernatant underwent the above operation for free fatty acid removal repeatedly 9 times. The final supernatant was concentrated on a rotary evaporator and further dried 24 hours under a reduced pressure of 5 mmHg to get 178 g of oily fraction. The above oily fraction was dissolved in 400 mL of acetone heated to 40° C. and kept 24 hours at 30° C. The precipitate was removed on G4 glass filter. After the filtrate was further kept 24 hours at 5° C., the precipitate was recovered on G4 glass filter, which was redissolved in 400 mL of acetone. The solution was kept 24 hours at 5° C. and the precipitate was recovered on G4 glass filter and washed with 100 mL of acetone on the same glass filter. Evaporation of remaining acetone under reduced pressure of 5 mmHg left 54 g of refined interesterified fat, which was analyzed by H P L C as in Example 2. Table 10 is the results.

TABLE 10

| | Composition - peak area (%) | | | | | |
|---|---|---|---|---|---|---|
| | FFA | DGs | TG molecular species | | | |
| | | | POP | SOP | SOS | Others |
| Palm kernel oil | 1.1 | 8.0 | 20.6 | 1.2 | 0 | 69.1 |
| Interesterified fat | 42.1 | 6.1 | 4.7 | 16.6 | 11.2 | 19.3 |
| After acid removal | 0.9 10.8 | 8.5 | 30.1 | 19.7 | 28.0 | |
| Refined fat | 0.1 | 4.1 | 13.2 | 40.2 | 32.4 | 8.5 |

Note:
DGs: diglycerides, FFA: free fatty acids, TG: triglyceride, P: palmitic acid, O: oleic acid, S: stearic acid.

Control 1

2.5 g of Lipase 3A (Lipase sp 225 from Mucor miehei immobilized on Duolite S761, supplied by Novo) was suspended in 50 mL of n-hexane and the resultant suspension was poured into a jacketed 150 mm long column 10 mm across in inside diameter for packing.

6 g of granulated CELITE was allowed to soak 2 mL of distilled water, with which another jacketed 150 mm long column 10 mm across was packed for use as the precolumn to adjust the moisture content of substrate solution. The same substrate solution as used in Example 1 was fed at a flow rate of 49.5 mL/hr to the above precolumn from below and the substrate solution output therefrom to the above immobilized lipase column from below. It is noted that the reaction system was kept at 45° C. The reaction solution was analyzed by the same methods as in Example 1 for the fatty acid composition of triglycerides and glyceride composition. Table 11 is the results.

TABLE 11

| | Interesterification by Lipase 3A | |
|---|---|---|
| Days | C18:0 (%) of fatty acid composition of TG | TG (%) of glyceride composition |
| 1 | 23.3 | 86.4 |
| 2 | 14.0 | 88.0 |
| 3 | 10.9 | 91.1 |

Table 11 shows that during the continuous process catalyzed by Lipase 3A in the same condition that applied when the DEAE-Toyopearl immobilized Lipase PL-679 preparation was used, the enzyme lost the activity thereof too quickly to produce interesterified oil or fat continuously, as indicated by the quickly decreasing in the proportion of fatty acid C18:0 in the fatty acid composition of triglycerides.

EXAMPLE 5

The same procedure as in Example 1 was repeated except that the flow rate of substrate solution was changed to 40.9 mL/hr (SV=3.5 hr$^{-1}$), 55.2 mL/hr (SV=4.7 hr$^{-1}$), 97.2 mL/hr (SV=8.3 hr$^{-1}$) or 150.5 mL/hr (SV=12.8 hr$^{-1}$). Table 12 is the results. It is noted that the moisture content of the reaction solution output from the immobilized enzyme column was always 200 ppm regardless of the flow rate.

Table 12 Interesterification at different flow rates

TABLE 12

| | | Interesterification at different flow rates | | | |
|---|---|---|---|---|---|
| Flow rate mL/hr | Days | Sa (%) in FA composition of TG | OA (%) in FA composition at 2-position | TG (%) in total composition | Percentage interesterification |
| 40.9 | 1 | 34.6 | 71.1 | 84.8 | 90 |
| | 3 | 34.4 | 70.2 | 82.4 | 90 |
| | 5 | 34.3 | 70.5 | 86.7 | 89 |
| 55.2 | 1 | 32.5 | 69.3 | 88.4 | 84 |
| | 3 | 32.0 | 70.3 | 88.1 | 83 |
| | 5 | 31.8 | 70.2 | 84.8 | 82 |
| 97.2 | 1 | 26.8 | 67.7 | 90.1 | 67 |
| | 3 | 26.0 | 69.8 | 88.1 | 66 |
| | 5 | 25.4 | 69.7 | 84.2 | 64 |
| 150.5 | 1 | 22.6 | 69.6 | 88.6 | 56 |
| | 3 | 22.5 | 69.7 | 85.4 | 56 |
| | 5 | 22.5 | 69.3 | 86.9 | 55 |

Note:
SA: stearic acid, OA: oleic acid, TG: triglycerides.

Table 12 shows that by changing the flow rate of substrate solution an arbitrary percentage interesterification can be selected. It is noted that the half life of the enzyme activity in interesterification was always about 190 days regardless of the flow rate of substrate solution. The amount of P O M F that 1 kg of the immobilized enzyme can process for 380 days, twice the half life of this enzyme preparation was calculated with the percentage interesterification set to 90, 84, 67 and 57% according to this Example and also to 94% according to Example 1. Table 13 is the results.

TABLE 13

| Percentage interesterification versus amount of raw material oil processed per kg of enzyme preparation | | |
|---|---|---|
| Percentage interesterification | SV (hr$^{-1}$) | Processed oil t/kg of immobilized enzyme* |
| 94 | 2.3 | 5.7 |
| 90 | 3.5 | 8.4 |
| 84 | 4.7 | 11.4 |
| 67 | 8.3 | 20.0 |
| 56 | 12.8 | 31.0 |

*Immobilized enzyme: DEAE-Toyopearl immobilized Lipase PL-679 with an activity of 100,000 U/g support.

EXAMPLE 6

The same procedure as in Example 1 was repeated except that the temperature of reaction system was kept at 50° C. Table 14 is the results. It is noted that the reaction solution output from the reactor column had a constant moisture content of 310 ppm.

TABLE 14

| | Interesterification at 50° C. | | | |
|---|---|---|---|---|
| Days | C18:0 (%) in FA composition of TG | C18:1 (%) at 2-position of TG | TG (%) in total composition | Percentage interesterification |
| 1 | 33.8 | 69.3 | 86.1 | 88 |
| 3 | 33.5 | 67.9 | 86.2 | 85 |
| 5 | 32.8 | 69.3 | 90.1 | 87 |
| 7 | 32.6 | 69.0 | 88.0 | 85 |

Note:
FA: fatty acid, TG: triglycerides.

Table 14 shows that also when the temperature of the reaction system was increased to 50° C. there was interesterification as satisfactory as in Example 1 where the temperature of the reaction system was set to 45° C.

EXAMPLE 7

2.5 g of dry DEAE-Toyopearl immobilized Lipase PL-679 preparation (100,000 U/g support) was suspended in 50 mL of n-hexane and the suspension was poured into a jacketed 150 mm long column 10 mm across in inside diameter for packing. On the other hand, 272.2 g of triolein and 200 g of trilaurin were dissolved in 660 g of n-hexane. The mixture was agitated with 1.59 g of distilled water. The substrate solution thus prepared had a moisture content of 1400 ppm. The reactor column packed with DEAE-Toyopearl immobilized Lipase PL-679 preparation was fed with the above substrate solution from below at a flow rate of 17.5 mL/hr while keeping the temperature of the reaction system at 45° C. While continuously feeding the column for consecutive 9 days, the reaction solution was sampled at intervals of 24 hours and analyzed for triglyceride molecular species by H P L C according to the same procedure as applied to Example 2. It is noted that the moisture content of the reaction solution output from the column stayed constant at 450 ppm. Table 15 is the results.

TABLE 15

| | Triglyceride molecular species of interesterified oil | | | | |
|---|---|---|---|---|---|
| TG molecular species | Substrate solution | Relative area (%) of peak | | | |
| | | 1st day | 3rd day | 5th day | 9th day |
| LLL | 42.3 | 14.4 | 14.3 | 14.7 | 16.9 |
| LLO | 0 | 23.3 | 23.3 | 22.7 | 22.9 |

TABLE 15-continued

| TG molecular species | Triglyceride molecular species of interesterified oil | | | | |
|---|---|---|---|---|---|
| | Substrate solution | Relative area (%) of peak | | | |
| | | 1st day | 3rd day | 5th day | 9th day |
| LOO | 0 | 32.5 | 32.6 | 32.6 | 29.1 |
| OOO | 57.4 | 19.1 | 19.0 | 19.7 | 20.7 |
| Others | 0.3 | 10.8 | 10.8 | 10.3 | 10.4 |

Note:
L: lauric acid, O: oleic acid, Others: diglycerides, free fatty acids, etc..

Table 15 shows that there was very satisfactory interesterification between different triglycerides, triolein and trilaurin in a continuous process.

EXAMPLE 8

A reactor column packed with DEAE-Toyopearl immobilized Lipase PL-679 preparation and a precolumn to adjust the moisture content of substrate solution were prepared according to the procedure as mentioned in Example 1.

177.2 g (5.6% w/v) of P O M F and 141.8 g of stearic acid (stearic acid/ P O M F=0.8 w/w) were dissolved in 1,850 g of n-hexane and the mixture was agitated with 5 mL of distilled water. After being left 30 minutes, the supernatant was used for the substrate solution. The immobilized enzyme column was continuously fed 9 consecutive days from below at a flow rate of 27.5 mL/hr with the above substrate solution after passage across the precolumn to adjust the moisture content of the solution to about 700 ppm. As in Example 1, the percentage interesterification was determined. The reaction temperature was 45° C. Table 16 includes the results (Run No. 1).

With 265.8 g (8.4% w/v) of P O M F and 212.7 g of stearic acid dissolved in 1,735 g of n-hexane, the same reaction as above was repeated to estimate the percentage interesterification thereby achieved. Table 16 includes the results (Run No. 2).

Further, with 443 g (14.0% w/v) of P 0 M F and 354.5 g of stearic acid dissolved in 1,500 g of n-hexane, the same reaction was repeated to estimate the percentage interesterification thereby achieved. Table 16 includes the results (Run No. 4).

Further, with 354.4 g of P O M F and 212.7 g of stearic acid (stearic acid/P O M F=0.6 w/w ) dissolved in 1,670 g of n-hexane, the same reaction was repeated to estimate the percentage interesterification thereby achieved. Table 16 includes the results (Run No. 5).

Further, with 354.4 g of P O M F and 141.8 g of stearic acid (stearic acid/P O M F=0.4 w/w dissolved in 1,720 g of n-hexane, the same reaction was repeated to estimate the percentage interesterification thereby achieved. Table 16 includes the results (Run No. 6). It is noted that the moisture content of the reaction solution output from the column was always kept at a constant level of 200 ppm.

TABLE 16

| Run No. | POMF concentration, % w/v | Ratio of SA* to POMF w/w | Percentage interesterification Day | | | | |
|---|---|---|---|---|---|---|---|
| | | | 1st | 3rd | 5th | 7th | 9th |
| 1 | 5.6 | 0.8 | 97 | 98 | 98 | 97 | 97 |
| 2 | 8.6 | 0.8 | 98 | 98 | 97 | 99 | 96 |
| 3* | 11.2 | 0.8 | 94 | 94 | 93 | 93 | 90 |
| 4 | 14.0 | 0.8 | 88 | 86 | 88 | 85 | 84 |
| 5 | 11.2 | 0.6 | 96 | 95 | 94 | 95 | 94 |
| 6 | 11.2 | 0.4 | 95 | 94 | 93 | 93 | 92 |

*SA: Stearic acid.
Note:
For Run No. 3, the procedure conformed to Example 1.

Table 16 shows that even if both the P O M F concentration and the ratio of stearic acid to P O M F are changed variously, there occurs very smooth interesterification in a continuous process almost without any change in the percentage interesterification.

EXAMPLE 9

50 g of Sepabead FP-DA05 (Mitsubishi Chemical Industries Co., Ltd.) was immersed 6 hours in 500 mL of aqueous 0.1N NaOH solution for activation. By filtration under suction, the activated Sepabead was collected on No. 1 filter paper and washed with 2 L of distilled water.

1 L of aqueous 5% Lipase PL-679 powder solution was agitated 4 hours at 4° C. with addition of 50 g of the above activated Sepabead for immobilization of the enzyme. By filtration under suction, the immobilized lipase preparation was collected on filter paper No. 1 and washed with 2 L of distilled water. Removal of moisture by freeze drying in vacuum produced 40 g of dry Sepabead FP-DA05 immobilized Lipase PL-679 preparation, which had an activity of 14,000 U/g support.

10 g of the above dry immobilized Lipase PL679 preparation was suspended in 100 mL of n-hexane and the suspension was poured into a 150 mm long column 20 mm across in inside diameter for packing.

On the other hand, after being allowed to soak up 2.5 mL of distilled water, 7 g of granulated celite was poured into a 150 mm long column 10 mm across in inside diameter to provide a precolumn to adjust the moisture content of the substrate solution. The same substrate solution as used in Example 1 was then passed across the precolumn and then across the immobilized enzyme column from below at the same flow rate of 27.5 mL/hr. The moisture content of the substrate solution was 700 and 200 ppm at the inlet and outlet, respectively, of the immobilized enzyme column. The above reaction system was kept at 45° C. for a continuous reaction of 9 days. The reaction solution output from the enzyme column was sampled at first, fourth, seventh and ninth days and analyzed by the methods of Example 1 for the glyceride composition and fatty acid composition of triglycerides. Table 17 is the results.

TABLE 17

| Day | Stearic acid (%) in fatty acid composition of TG | TG proportion (%) in glyceride composition |
|---|---|---|
| 1 | 32.1 | 89.3 |
| 4 | 31.9 | 90.2 |
| 7 | 31.9 | 90.1 |
| 9 | 31.7 | 89.5 |

Table 17 shows that the Sepabead FP-DA05 immobilized Lipase PL-679 preparation can catalyze interesterification in continuous process.

EXAMPLE 10

15 g of Duolite S761 was immersed in 500 mL of aqueous 1N NaOH solution. By filtration under suction, the resin was then recovered on filter paper No. 1 and washed with 1 L of distilled water until the pH of the filtrate reached 6.0. Filtration under suction was continued until excess water was removed from the resin. The resin was added to 300 mL of aqueous 1% Lipase PL-679 powder solution (which contained an enzyme activity of 300,000 U). The solution was then agitated 1 hour at 4° C. and left 12 hours. The recovered resin was a Duolite S761 immobilized Lipase PL-679 preparation. From the lipase activity that remained in the supernatant, the above immobilized lipase preparation was found to have an enzyme activity of 1,940 U/g dry resin.

Repeating the above procedure with use of Duolite A587 instead gave another immobilized Lipase PL-679 preparation having an enzyme activity of 1,710 U/g dry resin.

The reaction of Example 1 was repeated except for use of 2.5 g of one or the other of the above immobilized Lipase PL-679 preparations instead of DEAE-Toyopearl immobilized Lipase PL-679 preparation to estimate the percentage interesterification.

Further, 240 mg of Lipase PL-679 powder and 2 g of celite were mixed uniformly for enzyme immobilization. The reaction of Example 1 was again repeated using the above immobilized Lipase PL-679 preparation instead of DEAE-Toyopearl Lipase PL-679 preparation and changing the flow rate to 3.0 mL/hr (SV=0.52 hr$^{-1}$). The percentage interesterification thus achieved was also estimated. The reaction of Example 1 was further repeated using 2.5g of a chitosan immobilized Lipase PL-679 preparation, Prolacto immobilized Lipase PL-679 preparation, or cellulose acetate immobilized Lipase PL-679 preparation as prepared by the aforementioned Method 2 instead of DEAE-Toyopearl immobilized Lipase PL-679 preparation and changing the flow rate to 3.0 mL/hr (SV=0.52 hr$^{-1}$) to estimate the percentage interesterification. The reaction of Example 1 was repeated once more using 1 g of Lipase PL-679 powder as it was instead to estimate the same parameter. Table 18 is the results.

TABLE 18

| Support | Matrix | Activity U/g support | Percentage interesterification | | | |
|---|---|---|---|---|---|---|
| | | | 1st day | 3rd day | 5th day | 7th day |
| Duolite S761 | Phenol-formaldehyde | 1,940 | 0 | 0 | 0 | 0 |
| Duolite A587 | Phenol-formaldehyde | 1,710 | 0 | 0 | 0 | 0 |
| Celite | | (10,900) | 79 | 78 | 75 | 75 |
| Chitosan | | (10,000) | 94 | 94 | 92 | 92 |
| Prolacto | | (10,000) | 82 | 80 | 79 | 78 |
| Cellulose acetate | | (10,000) | 72 | 71 | 71 | 69 |
| PL-679 powder only | | (100,000) | 99 | 98 | 99 | 99 |

Table 18 shows that celite-, chitosan-, Prolacto-, and cellulose acetate immobilized Lipase PL-679 preparations as well as Lipase PL-679 powder catalyze the interesterification satisfactorily.

EXAMPLE 11

The reaction of Example 1 was repeated using the immobilized Lipase PL-266 preparation (10,000 U/g carrier), immobilized Lipase AL preparation (10,000 U/g carrier), and immobilized Lipase PS preparation (10,000 U/g carrier), respectively, all carried by DEAE-Toyopearl instead of DEAE-Toyopearl immobilized Lipase PL-679 preparation to estimate the percentage interesterification attained in each case. The same reaction as in Example 1 was also conducted with another DEAE-Toyopearl immobilized Lipase PL-679 preparation (100,000 U/g carrier) to estimate the above parameter. Table 19 shows the results. It is noted that regardless of which of the above four immobilized lipase preparations was used, the substrate solution was fed at a uniform flow rate of 3.0 mL/hr and the reaction solution output from the column had a uniform and constant moisture content of 210 ppm.

TABLE 19

| | Percentage interesterification Lipase type | | | |
|---|---|---|---|---|
| Days | PL-266 | AL | PS | PL-679 |
| 1 | 93 | 93 | 90 | 99 |
| 3 | 92 | 92 | 88 | 100 |
| 5 | 90 | 90 | 86 | 100 |
| 9 | 88 | 88 | 83 | 99 |

Table 19 shows that all of Lipases PL-266, AL and PS, when immobilized on DEAE-Toyopearl are applicable to interesterification in continuous process.

EXAMPLE 12

2.5 g of DEAE-Toyopearl immobilized Lipase PL-679 preparation (100,000 U/g support) was suspended in 50 mL of olive oil and poured into a jacketed 150 mm long column 10 mm across in inside diameter for packing. Meanwhile, 250 g of olive oil was heated to 45° C. with 100 g of capric acid to have a uniform solution, to which 0.29 mL of distilled water was further added for use as substrate solution (containing 1,040 ppm moisture). While keeping the reaction system at 40° C., the above substrate solution was pumped by a micropump at a flow rate of 4.1 mL/hr to feed the immobilized enzyme column from below. The reaction solution was sampled at intervals of 24 hours and analyzed by H P L C for molecular species of triglycerides using the same method as described in Example 2. Table 20 is the results. It is noted that the reaction solution output from the column was found to have a constant moisture content of 470 ppm.

TABLE 20

| | TG molecular species in reaction solution (% area) | | |
|---|---|---|---|
| Days | OOO | OOC | COC |
| 1 | 20.3 | 49.5 | 6.7 |
| 3 | 19.1 | 49.8 | 10.0 |

TABLE 20-continued

| Days | TG molecular species in reaction solution (% area) | | |
|---|---|---|---|
| | OOO | OOC | COC |
| 5 | 19.8 | 49.4 | 9.4 |
| 7 | 20.6 | 48.8 | 9.1 |
| Substrate | 60.2 | 0 | 0 |

Note:
O: Oleic acid, C: Capric acid, Substrate: Olive oil.

Table 20 shows that DEAE-Toyopearl immobilized Lipase PL-679 preparation is applicable to the interesterification without use of any organic solvent.

EXAMPLE 13

The DEAE-Toyopearl immobilized Lipase PL-679 column and precolumn to adjust the moisture content of the substrate solution were prepared as described in Example 1.

354.4 g of P O M F and 297.6 g of methyl stearate were dissolved in 1600 g of n-hexane. The solution was agitated with 5 mL of distilled water and then left 30 minutes to get supernatant for use as the substrate solution. The substrate solution was passed across the precolumn to adjust the moisture content to approx. 700 ppm and then the solution was fed to the immobilized enzyme column from below at a flow rate of 27.5 mL/hr for consecutive 9 days. All subsequent steps were executed in conformity to Example 1 and the percentage interesterification was estimated. It is noted that the reaction temperature was 45° C. Table 21 includes the results.

The same procedure as above was repeated except for use of 311.5 g of ethyl stearate or 339.6 g of butyl stearate instead of 297.6 g of methyl stearate to give individual estimates of the percentage interesterification achieved. Table 21 includes the results. It is noted that the reaction solution output from the column had a constant moisture content of 260 ppm.

TABLE 21

| | Interesterification in presence of a fatty acid ester | | |
|---|---|---|---|
| | Percentage interesterification | | |
| Days | Methyl stearate | Ethyl stearate | Butyl stearate |
| 1 | 74 | 73 | 76 |
| 3 | 75 | 75 | 74 |
| 5 | 71 | 70 | 74 |
| 7 | 69 | 70 | 73 |
| 9 | 68 | 67 | 71 |

Table 21 shows that the DEAE-Toyopearl immobilized Lipase PL-679 preparation can satisfactorily catalyze the transesterification of P O M F with a fatty acid ester, such as methyl stearate, ethyl stearate or butyl stearate, in continuous process.

EXAMPLE 14

The DEAE-Toyopearl immobilized Lipase PL-679 column and precolumn to adjust the moisture content of the substrate solution were prepared as described in Example 1.

350 g of olive oil and 350 g of coconut oil were dissolved in 1600 g of n-hexane. The solution was agitated with 5 mL of distilled water and left 30 minutes. The supernatant whose moisture content was 200 ppm was used for the substrate solution. After passage across the precolumn, the moisture content of the substrate solution increased to 550 ppm.

The above immobilized Lipase pL-679 column was fed from below with the substrate solution output from the precolumn at a flow rate of 27.5 mL/hr (SV=2.3 hr$^{-1}$). It is noted that the temperature of the reaction system was kept at 45° C. Feeding the column continuously for 7 days gave 4.6 L of the reaction solution.

The reaction solution was analyzed by H P L C for molecular species of triglycerides using the same method as described in Example 2. Table 22 is the results. It is noted that the reaction solution as output from the column had a constant moisture content of 130 ppm.

TABLE 22

| Molecular species of triglycerides of interesterified oil | | |
|---|---|---|
| | % area | |
| TG's carbon atoms | Interesterified oil | Substrate (olive oil + coconut oil) |
| 30 | 1 | 1 |
| 32 | 2 | 5 |
| 34 | 4 | 7 |
| 36 | 4 | 9 |
| 38 | 7 | 8 |
| Subtotal | 18 | 30 |
| 40 | 6 | 5 |
| 42 | 12 | 3 |
| 44 | 10 | 2 |
| 46 | 10 | 1 |
| 48 | 15 | 1 |
| Subtotal | 53 | 12 |
| 50 | 8 | 4 |
| 52 | 9 | 21 |
| 54 | 11 | 32 |
| 56 | 1 | 1 |
| Subtotal | 29 | 58 |

Table 22 shows that the DEAE-Toyopearl immobilized Lipase PL-679 preparation can satisfactorily catalyze the interesterification of a mixture of olive oil and coconut oil in continuous process.

EXAMPLE 15

A DEAE-Toyopearl immobilized Lipase PL-679 column and precolumn to adjust the moisture content of the substrate solution were prepared as described in Example 1.

560 g of palm oil and 840 g of soybean oil were dissolved in 3200 g of n-hexane. The solution was agitated with 10 mL of distilled water and left 30 minutes. The supernatant was used for the substrate solution. After passage across the precolumn, the substrate solution had a moisture content of 500 ppm.

In conformity to Example 14, the column was continuously fed with the above substrate solution for 7 days to get 4.6 L of the reaction solution. Evaporation of n-hexane from the reaction solution on a rotary evaporator under a reduced pressure of 20 mmHg left 1000 g of interesterified oil, which was cooled very slowly to reach 5° C. in 48 hours. Crystals that formed were filtered out at the same temperature. The liquid oil was produced at a yield of 85%. In a 24 hours cooling test in icy water of 0° C., the above liquid oil showed no sign of clouding. This means production of a cold resistant interesterified oil.

Further, 560 g of palm oil and 840 g of rapeseed oil were dissolved in 3200 g of n-hexane and 10 mL of distilled water was added to the solution. Using the supernatant, the above process of interesterification was repeated to get 1000 g of an interesterified glyceride oil. It is noted that the moisture content of the solution was 500 and 150 ppm, respectively, at the inlet and outlet of the column. The above interesterified oil was cooled very slowly to reach 5° C. in 48 hours. Crystals thus formed were filtered out at the same temperature. The liquid oil was produced at a yield of 88%, which stood a 24 hours cooling test. An interesterified glyceride oil that had a satisfactory resistance to cold was thus produced.

Further, 700 g of beef tallow and 700 g of olive oil were dissolved in 3200 g of n-hexane and 10 mL of distilled water was added to the solution. Using the supernatant, the above process of interesterification was repeated to get 1000 g of an interesterified glyceride oil. Also in this case, the moisture content of the solution was 500 and 150 ppm at the inlet and outlet, respectively, of the column. The above interesterified glyceride fat showed a melting point of 23° to 27° C. on a differential scanning calorimeter (Metler). A new fat could thus be produced by interesterification of a blend of beef tallow (melting point 40° to 50° C.) and olive oil (melting point −6° C.).

Further, 1400 g of shea olein (fractionated oil from shea fat) was dissolved in 3200 g of n-hexane and 10 mL of distilled water was added to the solution. Using the supernatant, the above process of interesterification was repeated to get 1000 g of an interesterified fat. Also in this case, the moisture content of the solution was 500 and 150 ppm, respectively, at the inlet and outlet of the reactor column. The above interesterified fat was analyzed by H P L C for molecular species of triglycerides using the same method as described in Example 2. Table 23 is the results.

TABLE 23

| Triglyceride molecular species | | | | |
|---|---|---|---|---|
| | TG molecular species (% area) | | | |
| | SOS | SLnS | SOO | Others |
| Interesterified shea olein | 21.0 | 5.3 | 41.7 | 32.0 |
| Raw material shea olein | 14.0 | 5.5 | 57.5 | 23.0 |

Note:
S: Stearic acid, O: Oleic acid, Ln: Linolic acid

Table 23 shows that the shea olein was successfully interesterified in continuous process.

EXAMPLE 16

A DEAE-Toyopearl immobilized Lipase PL-679 column and precolumn to adjust the moisture content of the substrate solution were prepared as described in Example 1.

354.4 g of olive oil and 204.8 g of palmitic acid were dissolved in 1600 g of n-hexane. The solution was agitated with 5 mL of distilled water and left 30 minutes. The supernatant was used for the substrate solution. The substrate solution whose moisture content was adjusted to 700 ppm by passage across the precolumn was fed to the above immobilized lipase column from below at a rate of 27.5 mL/hr. At intervals of 24 hours, the reaction solution was sampled and analyzed by H P L C for molecular species of triglycerides using the same method as described in Example 2. Table 24 is the results. It is noted that the reaction solution output from the column had a constant moisture content of 200 ppm.

TABLE 24

| | TG molecular species (% area) in reaction solution | | |
|---|---|---|---|
| Days | OOO | OOP | POP |
| 1 | 15.1 | 37.0 | 23.2 |
| 3 | 14.6 | 37.3 | 23.5 |
| 5 | 15.2 | 36.9 | 22.8 |
| 7 | 15.5 | 37.0 | 22.4 |
| Substrate | 60.2 | 14.6 | 0 |

Note:
O: Oleic acid, P: Palmitic acid, Substrate: Olive oil

Instead of 204.8 g of palmitic acid, 160 g of lauric acid was used to repeat the above process and analysis for triglyceride molecular species. It is noted that the reaction solution output from the column had a constant moisture content of 200 ppm. Table 25 is the results.

TABLE 25

| | TG molecular species (% area) | | |
|---|---|---|---|
| Days | OOO | OOL | LOL |
| 1 | 13.5 | 29.6 | 15.4 |
| 3 | 13.4 | 28.2 | 15.6 |
| 5 | 13.7 | 29.1 | 15.1 |
| 7 | 14.1 | 29.4 | 14.9 |
| Substrate | 60.2 | 0 | 0 |

Note:
O: Oleic acid, L: Laulic acid, Substrate: Olive oil

Tables 24 and 25 show that the DEAE-Toyopearl immobilized Lipase PL-679 preparation can satisfactorily catalyze the interesterification of olive oil with a fatty acid, such as palmitic acid or laulic acid in continuous process.

EXAMPLE 17

30.2 g of coconut oil and 14.9 g of oleic acid were dissolved in 144 g of n-hexane and 0.11 mL of distilled water was further added for full agitation. A substrate solution containing 600 ppm moisture was thus prepared.

An immobilized enzyme column prepared as described in Example 1 was then fed with the above substrate solution from below at a flow rate of 20 mL/hr. The reaction was continued 5 days at 40° C. From the whole volume of the reaction solution, a 0.1 mL sample was taken and dried under a stream of $N_2$ gas. After addition of 0.2 mL of TMSl-H (supplier: Gaschro Kogyo), the solid residue was heated 15 minutes at 60° C. for trimethylsilylation. The trimethylsilylated sample was analyzed by gas chromatography. Namely, on a 1 m long column 3 mm across in inside diameter packed with a packing material of JXR-Silicone3% (support Chromosorb WAW.DMCS supplied by Gaschro Kogyo), the above sample was chromatographed at a column temperature of 350° C. with carrier gas ($N_2$) fed at 40 mL/min to isolate individual components for detection by a hydrogen flame ionization detector. Table 26 is the results.

TABLE 26

| | Triglyceride composition, % w/w | | | | | | | | | | |
|---|---|---|---|---|---|---|---|---|---|---|---|
| | Number of carbons | | | | | | | | | | |
| | 30 | 32 | 34 | 36 | 38 | 40 | 42 | 44 | 46 | 48 | Others |
| Interesterified oil | 0.7 | 4.7 | 4.9 | 28.2 | 8.2 | 7.2 | 20.1 | 7.3 | 4.6 | 12.3 | 1.8 |
| Coconut | 1.4 | 8.6 | 7.5 | 51.8 | 7.3 | 8.5 | 8.2 | 1.4 | 1.4 | 1.3 | 2.6 |

TABLE 26-continued

| | Triglyceride composition, % w/w | | | | | | | | | | |
|---|---|---|---|---|---|---|---|---|---|---|---|
| | Number of carbons | | | | | | | | | | |
| | 30 | 32 | 34 | 36 | 38 | 40 | 42 | 44 | 46 | 48 | Others |
| oil | | | | | | | | | | | |

EXAMPLE 18

42.2 g of beef tallow and 6.4 g of arachidonic acid were dissolved in 211 g of n-hexane for use as the substrate solution.

According to Example 1, the above substrate solution was passed across the precolumn and then fed to an immobilized enzyme column from below at a flow rate of 15 mL/hr. The reaction was continued 3 days at 40° C. Also according to Example 1, the reaction solution was sampled, 1 mL each time, at intervals of 24 hours and analyzed by gas chromatography for the fatty acid composition of triglycerides. Table 27 is the results.

TABLE 27

| | Fatty acid composition (% w/w) of triglycerides | | | | |
|---|---|---|---|---|---|
| Day | PA | SA | OA | AA | Others |
| 1st | 21.6 | 24.2 | 34.2 | 12.2 | 7.8 |
| 2nd | 21.4 | 24.1 | 34.4 | 12.4 | 7.6 |
| 3rd | 21.4 | 24.2 | 34.0 | 12.2 | 8.2 |
| Tallow | 25.6 | 29.0 | 35.2 | 0 | 10.2 |

Note:
PA: Palmitic acid, SA: Stearic acid, OA: Oleic acid, AA: Arachidonic acid

Table 27 shows that it is possible to introduce highly unsaturated fatty acids into glyceride molecules according to the continuous process of interesterification of the invention.

EXAMPLE 19

302.4 g of coconut oil, 144.2 g of caprylic acid and 86.1 g of caproic acid were dissolved in 407 g of n-hexane and 0.55 mL of distilled water was further added to prepare a substrate solution containing 600 ppm moisture.

According to Example 1, an immobilized enzyme column was fed from below with the above substrate solution at a rate of 10 mL/hr. The reaction was continued 3 days at 40° C. From the whole volume of the reaction solution, a 0.1 mL sample was taken for the same analysis as done in Example 17. Table 28 shows the results.

EXAMPLE 20

40 g of DEAE-Toyopearl immobilized Lipase PL-679 preparation (100,000 U/g support, moisture content: 0.5%) was suspended in n-hexane and poured into a jacketed 500 mm long column 15 mm across in inside diameter for packing as in Example 1. Meanwhiles, 38 g of granulated CELITE, after being allowed to soak 30 g of distilled water, was poured in another jacketed column of the same dimensions for use as precolumn to adjust the moisture content of the substrate solution.

1,140 g of P O M F and 911 g of stearic acid were dissolved in 7,800 ml of n-hexane to provide the substrate solution, which was found to contain 120 ppm moisture. Part of the substrate solution was micropumped at a rate of 155 mL/hr to enter the precolumn from below to adjust the moisture content thereof to 750 ppm before entering a 50 mm long column 10 mm across in inside diameter packed with glass beads, each 1 mm across to join the remainder of the substrate solution that was pumped by micropump at a flow rate of 135 mL/hr to directly enter the above glass bead column. A substrate solution containing 400 ppm moisture that came out of the above glass bead column was poured in the immobilized lipase column from top for reaction at 50° C. The continuous process of interesterification was thus started.

For the first 3 days, during which the flow rate of the substrate solution was kept at 290 mL/hr, the reaction solution was sampled at intervals of 24 hours to determine the percentage interesterification achieved by the same method as applied to Example 1. The percentage interesterification was estimated to 98% on an average. From the fourth day on, the flow rate was slowly reduced from 290 mL/hr to reach 206 mL/hr at the end of a further 90 days reaction. The percentage interesterification during this 90 days period was found to stay in a range from 97.5 to 98.5%. It is noted that from the fourth day on the reaction solution was sampled at intervals of 3 days for the same analysis as above. Table 29 shows the results.

Figure 2:
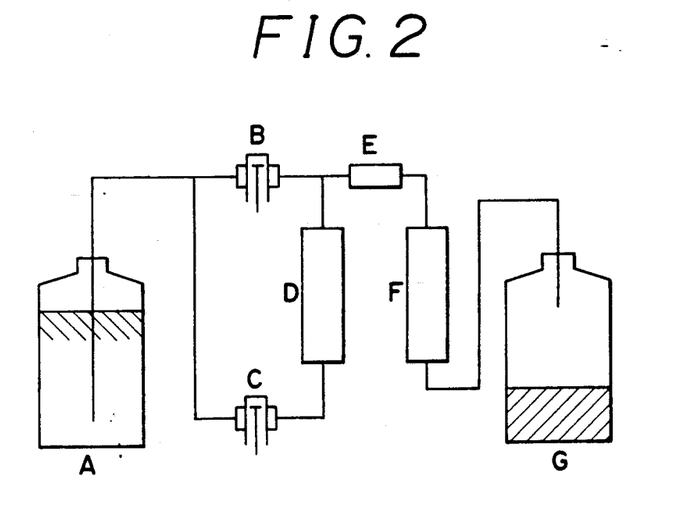
FIG. 2 is a flow sheet of an preferable example of the continuous process of interesterification embodying the invention.

FIG. 2 is a flow chart of the process of this example, wherein there are shown the substrate solution tank A, micropumps B, C, precolumn D to adjust the moisture content of the substrate solution, line mixer E, reactor column F packed with immobilized lipase, and product tank G. It is noted that the micropump B is run to add the original substrate solution to the one whose mois-

TABLE 28

| | Triglyceride composition (% w/w) | | | | | | | | | |
|---|---|---|---|---|---|---|---|---|---|---|
| | Number of carbons | | | | | | | | | |
| | 24 | 26 | 38 | 30 | 32 | 34 | 36 | 38 | 40 | 42 and over |
| Transesterified coconut oil | 10.7 | 4.0 | 14.1 | 8.5 | 17.4 | 11.5 | 20.8 | 5.6 | 3.0 | 4.4 |
| Raw coconut oil | 0.2 | 0.2 | 1.5 | 1.4 | 8.6 | 7.5 | 51.8 | 7.2 | 8.5 | 13.0 | ture content is adjusted by passage across the precolumn so as to readjust the moisture content of the substrate solution to an arbitrary level.

TABLE 29

| | Flow rate of substrate solution, mL/hr | % interesterification | TG proportion, % | Moisture, ppm of substrate solution at | |
|---|---|---|---|---|---|
| Days | | | | Column inlet | Column outlet |
| 1-3 | 290 | 98.0 | 95.5 | 400 | 162 |
| 6 | 280 | 97.5 | 96.1 | 405 | 154 |
| 12 | 274 | 97.6 | 96.3 | 423 | 148 |
| 18 | 267 | 97.8 | 95.9 | 408 | 155 |

TABLE 29-continued

| Days | Flow rate of substrate solution, mL/hr | % interesterification | TG proportion, % | Moisture, ppm of substrate solution at Column inlet | Moisture, ppm of substrate solution at Column outlet |
|---|---|---|---|---|---|
| 24 | 260 | 97.8 | 96.0 | 396 | 150 |
| 30 | 255 | 98.3 | 96.2 | 401 | 154 |
| 36 | 250 | 98.1 | 96.2 | 430 | 146 |
| 42 | 245 | 98.4 | 95.8 | 414 | 149 |
| 48 | 239 | 98.2 | 95.9 | 385 | 164 |
| 54 | 234 | 98.3 | 96.3 | 394 | 162 |
| 60 | 230 | 98.0 | 96.3 | 407 | 163 |
| 66 | 224 | 97.8 | 96.1 | 424 | 144 |
| 72 | 220 | 98.4 | 96.0 | 398 | 148 |
| 78 | 215 | 98.2 | 96.2 | 406 | 145 |
| 84 | 210 | 98.0 | 95.8 | 411 | 164 |
| 90 | 206 | 98.1 | 96.1 | 392 | 161 |

EXAMPLE 21

10 g of DEAE-Toyopearl immobilized Lipase PL-679 preparation (100,000 U/g support) was suspended in 100 mL of olive oil and poured in a 200 mm long column 15 mm across in inside diameter. 120 g of stearic acid was dissolved with 0.18 g of distilled water in 150 g of olive oil to get a substrate solution containing 970 ppm moisture. The immobilized enzyme column was fed from top with the above substrate solution at a flow rate of 12 g/hr while keeping the entire reaction system at 75° C. The reaction solution was sampled at intervals of 24 hours and analyzed for molecular species of triglycerides by H P L C by the same method as applied to Example 2. Table 30 is the results. It is noted that the reaction solution output from the column had a constant moisture content of 180 ppm.

TABLE 30

| Days | TG molecular species (% area) in reaction solution OOO | OOS | SOS |
|---|---|---|---|
| 1 | 23.5 | 32.7 | 13.1 |
| 3 | 24.0 | 31.0 | 12.2 |
| 5 | 24.1 | 30.8 | 12.4 |
| 7 | 24.4 | 30.3 | 12.2 |
| Substrate | 60.2 | 1.8 | 0.3 |

Note:
O: Oleic acid, S: Stearic acid, Substrate: Olive oil.

What is claimed is:

1. A continuous process for the interesterification of oils or fats comprising treating said oils or fats in the presence of a fatty acid wherein a reactor column packed with a lipase having a molecular weight of about 100 kD or greater as determined by fractionation on a Sephadex G200 column and an optimum pH of about 8.0 or greater, isolated from a species of microorganism selected from the group consisting of Alcaligenes and Achromobacter and containing 0 to 5% moisture, is fed with a substrate solution composed of said oils or fats and said fatty acid in such manner that said substrate solution which has a moisture content in the range of 100 to 1800 ppm is fed to said reactor column and the reaction solution output from said reactor column has a moisture content in the range of 50 to 800 ppm, the moisture content being adjusted to said ranges by passing said substrate solution across a precolumn packed with a hygroscopic solid that is moistened beforehand, before being fed to said reactor column.

2. A process as claimed in claim 1 wherein said interesterification proceeds without any operation for dehydration.

3. A process as claimed in claim 1 wherein said preparation is either a lipase product by itself or an immobilized lipase preparation that is prepared by a process selected from the group consisting of binding to an ion exchange resin or by mixing with proteins, sugars and/or mineral clay and drying.

4. A process as claimed in claim 3 wherein said ion exchange resin is a weakly basic methacrylate ion exchange resin.

5. A process as claimed in claim 1 wherein said alkaline high molecular weight lipase has a 1,3-positional specificity.

6. A process as claimed in claim 1 wherein said continuous reaction occurs at temperatures up to 80° C.

7. A process as claimed in claim 1 wherein the moisture content of said lipase preparation is adjusted by freeze drying.

8. A process as claimed in claim 1 wherein an interesterified oil or fat solution that forms by said reaction is cooled to precipitate components of higher melting points for removal or isolation.

9. A process as claimed in claim 8 wherein an alkali agent is added to said interesterified oil or fat solution for removal of free fatty acids as soap.

10. A process as claimed in claim 1 wherein said interesterified oil or fat solution is distilled under reduced pressure or filtered across membrane to remove solvent for recovery of a solvent-free interesterified oil or fat fraction.

11. A process as claimed in claim 10 wherein said solvent-free interesterified oil or fat fraction is redissolved in an organic solvent and cooled to precipitate interesterified oil or fat for refining.

12. A process as claimed in claim 10 wherein said solvent-free interesterified oil or fat fraction is distilled to remove free fatty acids and leave a refined interesterified oil or fat.

13. A process as claimed in claim 12 wherein said refined oil or fat is redissolved in an organic solvent and precipitated by cooling for further fractionation and refining.

* * * * *